US009020100B2

(12) United States Patent
Mastronardi et al.

(10) Patent No.: US 9,020,100 B2
(45) Date of Patent: *Apr. 28, 2015

(54) MULTIPLE IMAGE COLLECTION AND SYNTHESIS FOR PERSONNEL SCREENING

(71) Applicant: American Science and Engineering, Inc., Billerica, MA (US)

(72) Inventors: Richard Mastronardi, Medfield, MA (US); Dean Fleury, Littleton, MA (US); Jeffrey R. Schubert, Somverville, MA (US); Joseph DiMare, Wakefield, MA (US); Richard Schueller, Chelmsford, MA (US); Alexander Chalmers, Norwood, MA (US)

(73) Assignee: America Science and Engineering, Inc., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/057,564

(22) Filed: Oct. 18, 2013

(65) Prior Publication Data

US 2014/0044238 A1 Feb. 13, 2014

Related U.S. Application Data

(63) Continuation of application No. 13/047,878, filed on Mar. 15, 2011, now Pat. No. 8,605,859, which is a continuation of application No. 12/897,197, filed on Oct. 4, 2010, now abandoned, which is a continuation (Continued)

(51) Int. Cl.
*G01N 23/203* (2006.01)
*G01K 5/04* (2006.01)

(Continued)

(52) U.S. Cl.
CPC ........ *G01V 5/0008* (2013.01); *G01N 23/20083* (2013.01); *G01N 23/201* (2013.01); *G01N 23/203* (2013.01); *G01V 5/0016* (2013.01); *G01V 5/0025* (2013.01)

(58) Field of Classification Search
CPC .......... G01N 23/20083; G01N 23/201; G01N 23/203; G01V 5/0008; G01V 5/0016; G01V 5/0025
USPC ........................ 378/87, 88, 90, 146, 196, 197
See application file for complete search history.

(56) References Cited

U.S. PATENT DOCUMENTS

| 3,780,291 A | 12/1973 | Stein et al. ..................... 250/363 |
| 3,961,186 A | 6/1976 | Leunbach ..................... 250/272 |

(Continued)

FOREIGN PATENT DOCUMENTS

| EP | 0 261 984 | 3/1988 | ............. G01N 23/04 |
| EP | 0 864 884 | 9/1998 | ............... G01V 5/12 |

(Continued)

OTHER PUBLICATIONS

European Patent Office, International Search Report—International Application No. PCT/US1998/018642, Jul. 7, 1999 (2 pages).

(Continued)

*Primary Examiner* — Allen C. Ho
(74) *Attorney, Agent, or Firm* — Sunstein Kann Murphy & Timbers LLP

(57) ABSTRACT

An apparatus and method for inspecting personnel or their effects. A first and second carriage each carries a source for producing a beam of penetrating radiation incident on a given subject. A positioner provides for relative motion of each beam vis-à-vis the subject in a motion, the vertical component of which is one-way. A detector receives radiation produced by at least one of the sources after the radiation interacts with the subject.

13 Claims, 15 Drawing Sheets

Related U.S. Application Data of application No. 12/272,056, filed on Nov. 17, 2008, now Pat. No. 7,809,109, which is a continuation of application No. 11/737,317, filed on Apr. 19, 2007, now Pat. No. 7,505,562.

(60) Provisional application No. 60/988,933, filed on Nov. 19, 2007.

(51) Int. Cl.
| | | |
|---|---|---|
| *G01K 5/10* | (2006.01) | |
| *H05G 1/02* | (2006.01) | |
| *G01V 5/00* | (2006.01) | |
| *G01N 23/20* | (2006.01) | |
| *G01N 23/201* | (2006.01) | |

(56) References Cited

U.S. PATENT DOCUMENTS

| | | | |
|---|---|---|---|
| 3,971,948 A | 7/1976 | Pfeiler et al. | 250/445 T |
| 3,990,175 A | 11/1976 | Conway et al. | 46/135 A |
| 4,064,440 A | 12/1977 | Roder | 250/359 |
| 4,107,532 A | 8/1978 | MaCovski | 250/360 |
| 4,380,817 A | 4/1983 | Harding et al. | 378/87 |
| 4,525,854 A | 6/1985 | Molbert et al. | 378/89 |
| 4,578,806 A | 3/1986 | Grass et al. | 378/162 |
| 4,692,937 A | 9/1987 | Sashin et al. | 378/62 |
| 4,799,247 A | 1/1989 | Annis et al. | 378/87 |
| 4,809,312 A | 2/1989 | Annis | 378/146 |
| 4,825,454 A | 4/1989 | Annis et al. | 378/87 |
| 4,864,142 A | 9/1989 | Gomberg | 250/390.04 |
| 4,870,670 A | 9/1989 | Geus | 378/87 |
| 5,179,581 A | 1/1993 | Annis | 378/57 |
| 5,181,234 A | 1/1993 | Smith | 378/87 |
| 5,212,720 A | 5/1993 | Landi et al. | 378/206 |
| 5,247,561 A | 9/1993 | Kotowski | 378/87 |
| 5,394,454 A | 2/1995 | Harding | 378/86 |
| 5,430,787 A | 7/1995 | Norton | 378/87 |
| 5,638,420 A | 6/1997 | Armistead | 378/57 |
| 5,692,028 A | 11/1997 | Geus et al. | 378/57 |
| 5,692,029 A | 11/1997 | Husseiny et al. | 378/88 |
| 5,696,806 A | 12/1997 | Grodzins et al. | 378/86 |
| 5,763,886 A | 6/1998 | Schulte | 250/358.1 |
| 5,764,683 A | 6/1998 | Swift et al. | 378/57 |
| 5,910,973 A | 6/1999 | Grodzins | 378/57 |
| 5,940,468 A | 8/1999 | Huang et al. | 378/57 |
| 5,974,111 A | 10/1999 | Krug et al. | 378/57 |
| 6,018,562 A | 1/2000 | Willson | 378/9 |
| 6,057,761 A | 5/2000 | Yukl | 340/568.1 |
| 6,081,580 A | 6/2000 | Grodzins et al. | 378/87 |
| 6,094,472 A | 7/2000 | Smith | 378/86 |
| 6,151,381 A | 11/2000 | Grodzins et al. | 378/90 |
| 6,192,104 B1 | 2/2001 | Adams et al. | 378/90 |
| 6,212,251 B1 | 4/2001 | Tomura et al. | 378/15 |
| 6,236,709 B1 | 5/2001 | Perry et al. | 378/57 |
| 6,249,567 B1 | 6/2001 | Rothschild et al. | 378/86 |
| 6,282,264 B1 | 8/2001 | Smith et al. | 378/189 |
| 6,301,326 B2 | 10/2001 | Bjorkholm | 378/57 |
| 6,375,697 B2 | 4/2002 | Davies | 55/340 |
| 6,421,420 B1 | 7/2002 | Grodzins | 378/98.6 |
| 6,442,233 B1 | 8/2002 | Grodzins et al. | 378/57 |
| 6,459,761 B1 | 10/2002 | Grodzins et al. | 378/57 |
| 6,473,487 B1 | 10/2002 | Le | 378/57 |
| 6,567,496 B1 | 5/2003 | Sychev | 378/57 |
| 6,628,745 B1 | 9/2003 | Annis et al. | 378/21 |
| 6,665,373 B1 | 12/2003 | Kotowski et al. | 378/90 |
| 6,754,304 B1 | 6/2004 | Kumakhov | 378/45 |
| 6,785,360 B1 | 8/2004 | Annis | 378/137 |
| 6,876,719 B2 | 4/2005 | Ozaki | 378/7 |
| 6,879,657 B2 | 4/2005 | Hoffman | 378/7 |
| 6,891,381 B2 | 5/2005 | Bailey et al. | 324/644 |
| 6,990,175 B2 | 1/2006 | Nakashima et al. | 378/65 |
| 7,203,276 B2 | 4/2007 | Arsenault et al. | 378/87 |
| 7,265,709 B2 | 9/2007 | Fleisher et al. | 342/22 |
| 7,305,062 B2 | 12/2007 | Hambüchen et al. | 378/9 |
| 7,400,701 B1 | 7/2008 | Cason | 378/57 |
| 7,460,636 B2 | 12/2008 | Ein-Gal | 378/9 |
| 7,476,023 B1 | 1/2009 | Canfield et al. | 378/203 |
| 7,505,562 B2 | 3/2009 | Dinca et al. | 378/87 |
| 7,551,715 B2 | 6/2009 | Rothschild et al. | 378/57 |
| 7,561,666 B2 | 7/2009 | Annis | 378/87 |
| 7,593,506 B2 * | 9/2009 | Cason | 378/90 |
| 7,639,866 B2 | 12/2009 | Pomero et al. | 382/154 |
| 7,796,733 B2 * | 9/2010 | Hughes | 378/87 |
| 7,796,734 B2 | 9/2010 | Mastronardi et al. | 378/90 |
| 7,806,589 B2 | 10/2010 | Tashman et al. | 378/197 |
| 7,809,109 B2 | 10/2010 | Mastronardi et al. | 378/90 |
| 7,826,589 B2 | 11/2010 | Kotowski et al. | 378/57 |
| 8,199,996 B2 * | 6/2012 | Hughes | 382/132 |
| 8,605,859 B2 * | 12/2013 | Mastronardi et al. | 378/90 |
| 2004/0057554 A1 | 3/2004 | Bjorkholm | 378/143 |
| 2004/0140924 A1 | 7/2004 | Keller et al. | 342/22 |
| 2005/0190878 A1 | 9/2005 | De Man et al. | 378/9 |
| 2005/0232397 A1 | 10/2005 | Atzinger et al. | 378/163 |
| 2007/0009088 A1 | 1/2007 | Edic et al. | 378/62 |
| 2007/0086564 A1 | 4/2007 | Bruder et al. | 378/9 |
| 2007/0258562 A1 | 11/2007 | Dinca et al. | 378/62 |
| 2010/0067654 A1 | 3/2010 | Kotowski et al. | 378/57 |
| 2011/0164726 A1 | 7/2011 | Mastronardi et al. | 378/62 |

FOREIGN PATENT DOCUMENTS

| | | | |
|---|---|---|---|
| EP | 1 168 249 | 1/2002 | G06T 17/00 |
| GB | 1 505 498 | 3/1978 | G01N 23/06 |
| GB | 2 277 013 | 10/1994 | G01N 23/04 |
| GB | 2 452 620 | 3/2009 | G01V 5/00 |
| JP | 62-147349 | 7/1987 | G01N 23/02 |
| WO | WO 98/02763 | 1/1998 | G01V 5/00 |
| WO | WO 98/03889 | 1/1998 | G01V 5/00 |
| WO | WO 98/20366 | 5/1998 | G01T 1/29 |
| WO | WO 99/13323 | 3/1999 | G01N 23/04 |
| WO | WO 01/59485 | 8/2001 | G01V 5/00 |
| WO | WO 03/012414 | 2/2003 | G01N 23/00 |

OTHER PUBLICATIONS

European Patent Office, International Preliminary Examination Report—International Application No. PCT/US1998/018642, Jul. 13, 1999 (3 pages).

European Patent Office, International Search Report—International Application No. PCT/US1999/028266, Sep. 6, 2000 (3 pages).

European Patent Office, International Search Report—International Application No. PCT/US1999/028035, Sep. 15, 2000 (3 pages).

European Patent Office, Written Opinion—International Application No. PCT/US1999/028035, Sep. 15, 2000 (4 pages).

European Patent Office, International Preliminary Examination Report—International Application No. PCT/US1999/028035, Mar. 25, 2002 (3 pages).

European Patent Office, International Search Report and Written Opinion of the International Searching Authority—International Application No. PCT/US2005/011382, Oct. 21, 2005 (8 pages).

European Patent Office, International Preliminary Report on Patentability, International Application No. PCT/US2005/011382, Oct. 11, 2006 (6 pages).

European Patent Office, International Search Report, International Application No. PCT/US2007/066936, Sep. 30, 2008 (5 pages).

European Patent Office, Written Opinion of the International Searching Authority, International Application No. PCT/US2007/066936, Sep. 30, 2008 (6 pages).

European Patent Office, Partial International Search Report—International Application No. PCT/US2008/083741, International Searching Authority, Aug. 4, 2009 (3 pages).

European Patent Office, International Search Report—International Application No. PCT/US2008/083741, Oct. 30, 2009 (5 pages).

Chou, "Fourier coded-aperture imaging in nuclear medicine", *IEEE Proc. Sci. Meas. Technol.*, vol. 141. No. 3, May 1994, pp. 179-184.

Mertz et al., "Rotational aperture synthesis for x-rays", *J. Opt. Soc. Am. A.*, vol. 3, No. 12, Dec. 1986, pp. 2167-2170.

Chen et al., "*Imaging for Concealed Weapon Detection*", Signal Processing Magazine, IEEE, vol. 22, Issue: 2, Mar. 2005 (10 pages). Collins et al., "*Ultra Wide Band Millimeter Wave Holographic 3-D*

(56) References Cited

OTHER PUBLICATIONS

*Imaging of Concealed Targets on Mannequins*", 1994 Review of Progress in Quantitative Nondestructive Evaluation Conference, Snowmass, CO (United States), Jul. 31-Aug. 5, 1994 (7 pages).
Smith, *"Bodysearch technology uses X-ray imaging to remove hazards and humiliation from personnel searches"* (Abstract), Security Technology, Proceedings of Institute of Electrical and Electronics Engineers 29th Annual 1995 International Carnahan Conference, Oct. 1995 (1 page).
Kotowski's Substantive Motion 1.
Kotowski's Substantive Motion 2.
Mastronardi's Responsive Motion 1.
Mastronardi's Opposition to Kotowski's Substantive Motion 2.
Kotowski's Opposition 1.
Mastronardi's Opposition to Kotowski's Substantive Motion 1.
Exhibit 1001 Declaration to Dr. Rudolph in Support of Mastronardi's Responsive Motion 1.
Exhibit 1003 Declaration of Dr. Zamenhof in Support of Mastronardi's Responsive Motion 1.
Exhibit 1039 Deposition Transcript of Dr. Larry Rudolph on Mar. 20, 2013.
Exhibit 1040 Deposition Transcript of Dr. Robert Zamenhof on Mar. 20, 2013.
Exhibit 1041Declaration of Dr. Larry Rudolph in Support of Mastronardi's Opposition to Kotowski's Substantive Motion 1.
Exhibit 1042 Declaration of Dr. Robert Zamenhof in Support of Mastronardi's Opposition to Kotowski's Substantive Motion 1.
Exhibit 1043 Declaration of Dr. Larry Rudolph in Support of Opposition to Kotowski's Substantive Motion 1.
Exhibit 1044 Declaration of Robert Zamenhof in Support of Mastronardi's Opposition to Kotowski's Substantive Motion 2.
Exhibit 2002 Declaration of Dr. Kia in Support of Kotowski's Substantive Motion 1.
Exhibit 2002 Declaration of Dr. Kia in Support of Kotowski's Substantive Motion 2.
Exhibit 2012 Deposition transcript of Dr. Omid Kia on Mar. 15, 2013.
Deposition Transcript of Dr. Kia on Jun. 7, 2013.

* cited by examiner

MULTIPLE IMAGE COLLECTION AND SYNTHESIS FOR PERSONNEL SCREENING

CROSS REFERENCE TO RELATED APPLICATIONS

The present application is a continuation of U.S. patent application Ser. No. 13/047,878, filed Mar. 15, 2011, now U.S. Pat. No. 8,605,859, which is a continuation of U.S. patent application Ser. No. 12/897,197, filed Oct. 4, 2010, which is a continuation of U.S. patent application Ser. No. 12/272,056, filed Nov. 17, 2008, which issued as U.S. Pat. No. 7,809,109, which claims priority to U.S. Provisional Application No. 60/988,933, filed Nov. 19, 2007. U.S. patent application Ser. No. 12/272,056 is also a continuation-in-part application of U.S. patent application Ser. No. 11/737,317, now U.S. Pat. No. 7,505,562, filed Apr. 19, 2007.

U.S. patent application Ser. No. 12/272,056 is also related to U.S. patent application Ser. No. 12/171,020, now U.S. Pat. No. 7,593,506, filed Jul. 10, 2008, which is a continuation application of U.S. patent application Ser. No. 11/097,092, filed Apr. 1, 2005 and issued Jul. 15, 2008 as U.S. Pat. No. 7,400,701. The present application, is also related to, U.S. Provisional Application No. 60/561,079, filed Apr. 9, 2004 and to U.S. Provisional Application No. 60/794,295, filed Apr. 21, 2006.

All of the foregoing applications and patents are hereby incorporated by reference herein in their entireties.

TECHNICAL FIELD AND BACKGROUND ART

The present invention relates to the field of x-ray imaging of personnel, packages, or other subjects to detect concealed objects.

Current personnel screening systems using backscatter and millimeter wave technology can provide images representative of the surface of the scanned subject, but, insofar as they may well not penetrate the entirety of the scanned subject, they lack the capability to image items of interest located on the far side of the subject, or items of interest that return a signal response similar to the background surrounding the subject, or items artfully concealed on the subject.

In an attempt to increase the detection accuracy of such screening systems, additional scans are required that might further necessitate repositioning the subject to be scanned. These additional scanning requirements, while possibly increasing detection accuracy, significantly reduce the rate of throughput of such systems that are generally implemented under circumstances that experience large volumes of scanning.

A system that provides both accurate and effective imaging at a high throughput rate and requires inspected subjects to be exposed to only a low dose of radiation is particularly desirable in such applications.

Accordingly, the present invention is directed toward providing an apparatus and method of scanning that can achieve these desired objectives.

SUMMARY OF EMBODIMENTS OF THE INVENTION

In accordance with preferred embodiments of the present invention an apparatus is provided that ascertains a material feature associated with a subject, and in certain embodiments, generates one or more images of the subject. The apparatus generally includes a first carriage, a second carriage, at least one vertical positioner, and at least one detector. Each carriage includes a source that is adapted to produce a beam of penetrating radiation incident on the subject. The vertical positioner is adapted to synchronously displace each carriage with respect to the subject in a direction having a vertical component. The at least one detector receives radiation produced by at least one of the sources after interaction of the radiation with the subject. The detector may be disposed on the first carriage. The subject may be a person.

The penetrating radiation produced by each source may be in the form of x-ray radiation. Each source may be adapted to produce a pencil beam of radiation. Each source may also have a scanner adapted to move the beam of penetrating radiation produced by the source transverse to the direction of motion of the carriages. Each scanner may be in the form of a chopper wheel and the chopper wheel may be adapted to provide interleaved beams.

Each carriage may include a plurality of detectors. Each plurality of detectors may include at least one of a scatter and transmission detector.

The first and second carriages may produce substantially oppositely directed beams of penetrating radiation.

The transmission detector of the first carriage may be disposed at an elevation substantially equal to that of the source of the second carriage.

In one embodiment of the present invention the first and second carriages may be structurally coupled. Both carriages may be coupled to a single mechanical platform wherein the at least one positioner is adapted to move the single mechanical platform in a direction having a vertical component.

In another embodiment of the present invention each source may be an intermittently irradiating source providing a temporally interlaced irradiation pattern.

An embodiment of the present invention may include a displacement encoder.

The positioner of the apparatus may include at least one of a rotary motor coupled to a lead screw, a rack and pinion system, an electromechanically propelled system, a hydraulic piston or a pulley system in accordance with an embodiment of the present invention.

The apparatus may include a processor for receiving a signal from the at least one detector and for producing an image based at least on the signal and may further include a processor for electronically combining the images produced by each detector in one embodiment.

In accordance with a related embodiment of the present invention the apparatus may include an enclosure for containing the carriages and the at least one positioner during the course of operation. At least one stationary detector may be coupled to the enclosure. The enclosure may be an environmentally controlled enclosure. The enclosure may be sealable from an external environment.

In an embodiment of the present invention each source may be a pulsed source adapted to intermittently irradiate the subject.

In accordance with another embodiment of the present invention an apparatus for ascertaining a material feature associated with a subject is provided that includes a first carriage, a second carriage and at least one vertical positioner. The first carriage includes a source adapted to produce a beam of penetrating radiation incident on the subject and a first detector for detecting penetrating radiation scattered by the subject. The second carriage includes a second detector for detecting penetrating radiation produced by the source of the first carriage and transmitted through the subject. The at least one vertical positioner is adapted to synchronously vary the position of each carriage with respect to the subject in a direction having a vertical component. The positioner may act on the first carriage to vary the relative position of the source on the first carriage with respect to the subject.

In accordance with another embodiment of the present invention an apparatus is provided for ascertaining a material feature associated with a subject. The apparatus includes two vertically disposed arrays of sources adapted to produce beams of penetrating radiation, at least one detector for receiving radiation produced by at least one of the sources after interaction of the radiation with the subject, and a controller for activating at least one source in at least one of the arrays independent from the other sources in the same array.

In a related embodiment the at least one detector of the apparatus includes two vertical arrays of detectors and a processor for processing detection data received by each detector during a specified time interval.

In another related embodiment the apparatus includes a scanner adapted to move at least one beam of penetrating radiation produced by at least one of the sources.

In accordance with another embodiment of the present invention a method is provided for inspecting a subject. The method has steps of: moving a first carriage having coupled to it a first source adapted to produce a beam of penetrating radiation incident on the subject, moving in synchronization with the first carriage a second carriage having coupled to it a second source adapted to produce a beam of penetrating radiation, detecting with at least one detector radiation produced by at least one of the sources after interaction of the radiation with the subject, generating detector output signals based on radiation received by the at least one detector, and characterizing the subject on the basis of the detector output signals. The at least one detector may be coupled to at least one of the first carriage and the second carriage.

In a related embodiment the method further includes scanning the beam of penetrating radiation produced by the source in a direction transverse to the direction of motion of the carriages.

In another related embodiment the method further includes creating an image based on radiation detected by the first and second detectors.

In yet another related embodiment the method include the steps of: scanning the beam of penetrating radiation produced by the source coupled to the second carriage in a direction transverse to the direction of motion of the carriages, generating detector output signals based on radiation received by the first and second detectors and creating an image based on radiation detected from the first and the second beam. In any of the described methods for inspecting a subject the subject may be a person.

In accordance with another embodiment of the present invention a method is provided for inspecting a subject. The method includes generating beams of penetrating radiation at a temporally varying elevation, the beams of penetrating radiation generated by at least one first source positioned to direct the radiation in a first direction toward the subject and at least one second source positioned to direct penetrating radiation in a second direction toward the subject and detecting with at least one detector the radiation produced by at least one of the sources after interaction of the radiation with the subject. The at least one first source may comprise a first plurality of sources disposed at distinct vertical heights and the at least one second source may comprise a second plurality of sources at distinct vertical heights.

BRIEF DESCRIPTION OF THE DRAWINGS

The present invention relates to the field of screening cargo or any other packages and/or subjects.

The foregoing features of the invention will be more readily understood by reference to the following detailed description taken with the accompanying drawings.

DETAILED DESCRIPTION OF PREFERRED EMBODIMENTS

Definitions

As used in this description and the accompanying claims, the following terms shall have the meanings indicated, unless the context otherwise requires:

A "carriage" is a moveable system including a source and/or a detector of penetrating radiation. A carriage may include a detector that detects radiation; however, it is not required to.

A "vertical positioner" is a system component capable of displacing a carriage in a direction having a vertical component. A positioner may include an actuator, such as a motor, and attendant mechanical linkages or couplings.

A "vertically disposed array" is a plurality of objects, generally sources or detectors, disposed in a configuration having a vertical component such that at least one source in a vertically disposed array of sources is at a different elevation than at least one other source in the same vertically disposed array.

Related application Ser. No. 12/687,762, filed Jan. 14, 2010, which issued as U.S. Pat. No. 7,796,734, is hereby incorporated by reference herein in its entirely.

Figure 1:
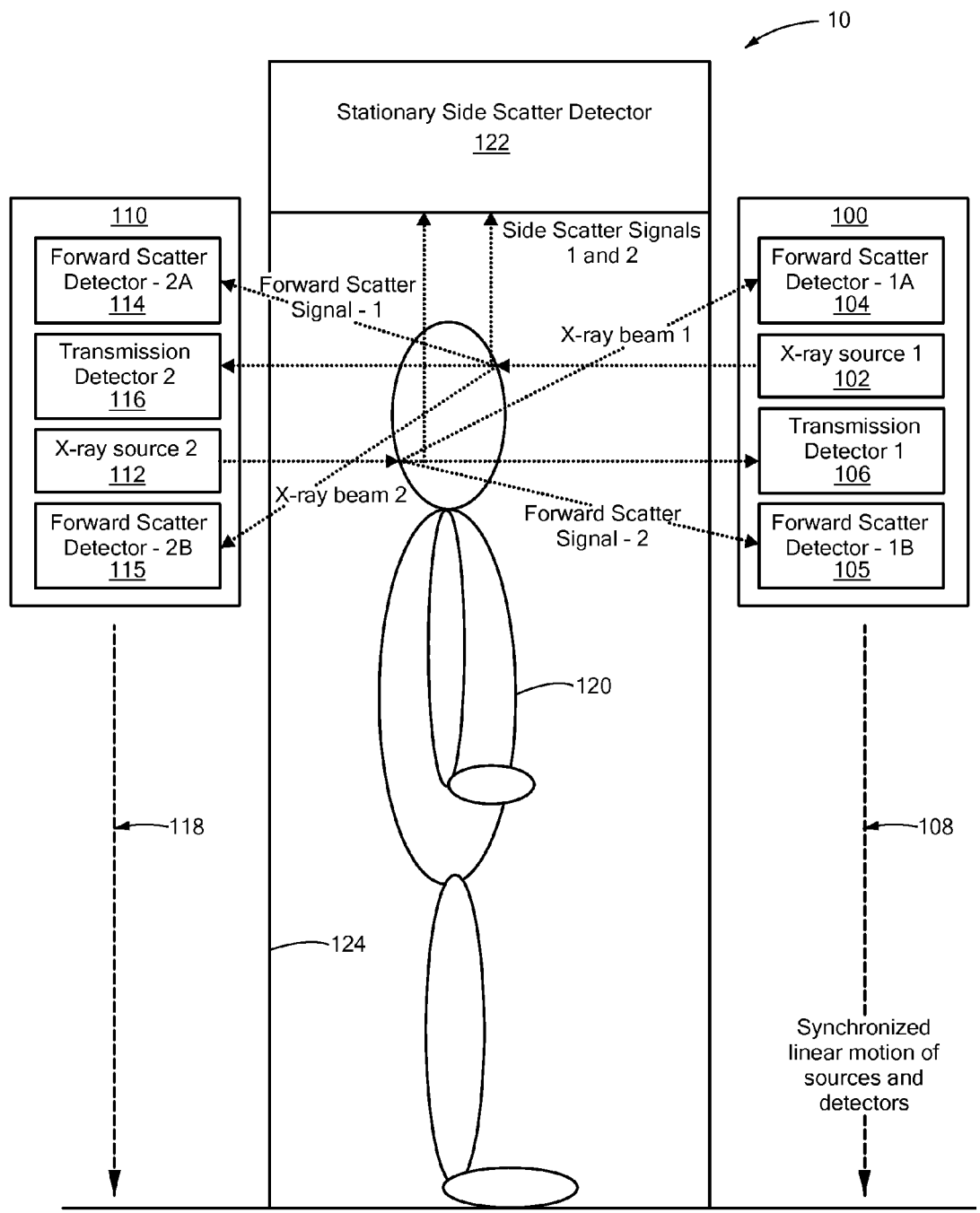
FIG. 1 is a schematic view of an embodiment of the present invention used to scan a person who has entered the imaging apparatus.

FIG. 1 is a schematic view of an embodiment of the present invention scanning a person who has entered a vicinity of the imaging apparatus. The imaging apparatus, illustrated in FIG. 1, and designated generally by numeral 10, uses two distinct sources that produce penetrating radiation so that the subject is scanned, in a single pass, and is imaged from two opposite sides, thereby enabling effective identification of any concealed objects. The penetrating radiation produced by each source is typically electromagnetic radiation, such as x-rays or sub-millimeter-wave radiation; however, under certain circumstances, the use of either electromagnetic radiation in other frequency ranges or of entirely different particles, such as baryons, may be advantageous. The sources are distinct in that they allow a beam of penetrating radiation to be produced from each carriage to facilitate imaging the subject. Various images may be produced including images based on transmission and/or scatter radiation detected on either side and/or top of the subject. These images may be produced contemporaneously. The contemporaneously produced images may be combined using any processing methods. Source 102 of the imaging apparatus 10 is coupled to carriage 100. Carriage 100 may include one or more detectors. Three detectors are shown for illustrative purposes. The three detectors illustrated include detector 104, configurable for forward scatter detection, detector 106, configurable for transmission detection, and detector 105, also configurable for forward scatter detection. It will be appreciated by those of ordinary skill in the art that carriages are not limited to including three detectors or a specific type of detector. Particularly, each detector may be configured to detect more than one form of radiation. A carriage may include one or more detectors and any single detector on the carriage may be configured to serve as a forward scatter, transmission, or backscatter radiation detector.

Configuring a detector to sense a particular kind of radiation may be achieved by modifying the detectors output, detection period, and/or sensitivity level. For example, each detector may output detected information to a processor specifically configured to process the detected signal. Further, the processor configuration may alternate depending on what type of radiation is detected during any given time interval. The detectors may be configured, for example, so that during the course of the time interval during which source 102 is producing a beam of radiation, detectors 104, 105, and 106 are configured to detect backscatter radiation, detectors 114 and 115 are configured to detect forward scatter radiation, and detector 116 is configured to detect transmission radiation. In the same example the detectors may be configured such that during the course of another time interval, defined by source 112 producing a beam of radiation, detectors 114, 115, and 116 are configured to detect backscatter radiation, detectors 104 and 105 are configured to detect forward scatter radiation, and detector 106 is configured to detect transmission radiation. This is just a single example of how the detectors may be configured to operate and the configuration is amenable to the provided system components and particular application. As such, various configurations, which may not be explicitly described may be provided in accordance with embodiments of the present invention.

Carriage 110, similar to carriage 100, includes three detectors that are coupled to it. The three detectors coupled to carriage 110 include detector 114 configurable to detect forward scatter radiation, detector 116 configurable to detect transmission radiation, and detector 115 also configurable to detect forward scatter detection. These detectors, as those on carriage 100, may each be configured, as discussed in the example above, to detect each type of radiation, including forward scatter, transmission, and/or backscatter radiation.

Carriages 100 and 110 are each maintained at substantially the same elevation throughout a scan. Carriages 100 and 110 are generally each coupled to separate vertical positioners that move the carriages along the trajectory illustrated by lines 108 and 118 respectively, as further illustrated in FIG. 2A. The positioners move the carriages 100 and 110 in a generally vertical direction at the same rate such that the carriages maintain a substantially equivalent elevation relative to one another throughout the displacement of each carriage. The imaging apparatus 10 illustrated further includes a stationary side scatter detector 122 that detects radiation scattered approximately vertically during a scan.

As the source illustrated in FIG. 1 scans subject 120 horizontally, simultaneous to the carriages 100 and 110 being displaced vertically in synchronization with one another, the radiation produced from a first source that is located on a first carriage may be detected, after interaction of the radiation with the subject 120, by detectors located on an opposing second carriage. Additionally, the radiation produced from a second source located on a second carriage may be detected, after interaction of the radiation with the subject 120, by detectors located on the opposing first carriage. The type of radiation detection may include transmission and or scatter detection. Although backscatter detectors are not expressly demonstrated on the carriages 100 and 110 in FIG. 1, the carriages 100 and 110 may include detectors configured to detect backscatter radiation. In an embodiment in which a detector is configured to detect backscatter radiation, the detector may detect radiation produced from a source located on the same carriage as the detector, as explained in the example above.

In a preferred embodiment the source of each carriage may be adapted to produce pencil beam x-rays. This may be achieved through the use of a collimator or by any means of producing a narrow beam of penetrating radiation. The source may be further adapted in a preferred embodiment to scan a subject 120 in a direction transverse to the generally vertical direction of travel by the carriage. The scanning may be achieved using devices including, but not limited to, chopper wheels, electromagnetic steering devices, or any other scanning systems.

FIG. 1 also illustrates the relative positions of the detectors on one carriage with respect to the source on an alternative carriage, specifically for the configuration of sources and detectors demonstrated. In the embodiment illustrated in FIG. 1, each source is located at a position that corresponds to the height or elevation of the opposing detector that is configurable for transmission detection. Specifically, detector 116 of carriage 110 is at substantially the same elevation as source 102 on carriage 100 and vice versa for source 112 on carriage 110 and detector 106 on carriage 100.

Two of the detectors configurable to detect forward scatter radiation on each carriage are disposed, in an embodiment, at a vertically offset distance from the corresponding source, such that the scattered radiation that results from the beam of penetrating radiation incident on the subject is detected. Although detector 106 may be configured to detect scatter radiation, detectors 104 and 105 may be more optimal than detector 106 at detecting forward scatter radiation resulting from the beam of source 112 interacting with a subject 120 disposed between the carriages 100 and 110. Similarly, detector 116 may be configured to detect forward scatter radiation, but detectors 114 and 115 may be more optimal than detector 116 at detecting forward scatter radiation resulting from the beam produced by source 102 interacting with a subject 120 due to the vertical offset of detectors 114 and 115 from source 102.

To achieve coordinated motion of the carriages, structural coupling that allows the carriage to move as a single body may be provided.

In use, a subject 120 enters a vicinity of the imaging apparatus 10 and then the carriages 100 and 110 are displaced vertically as the subject 120 is scanned from at least two sides in a single pass. As a new subject 120 enters the portal for scanning, the carriages 100 and 110 can begin scanning the subject 120 from their current position as they are displaced vertically in the opposite direction of displacement performed in the previous scan. For example, one subject 120 is scanned as the carriages 100 and 110 are displaced in a vertical direction decreasing in elevation and after the scan is completed and the next subject enters, the next subject may be scanned as the carriages 100 and 110 are displaced in a vertical direction increasing in elevation.

In another embodiment of the present invention each carriage may include a source without any detectors coupled to the moveable carriage. For example, carriages 100 and 110 may each be provided without any of detectors 104, 105, 106, 114, 115, and 116. In this example, stationary detectors may be provided that detect transmission and/or scatter radiation as the carriages 100 and 110 are displaced and the sources alternate activation. The stationary detectors in this example may still be configurable. The stationary detectors may also be provided, for example, in an array that extends approximately the length of travel of the carriages 100 and 110, thereby allowing them to detect radiation similar to the detectors attached to the carriages 100 and 110 illustrated in FIG. 1.

While FIG. 1 generally illustrates each carriage as having a source, it is within the scope of the current invention to provide a source on only one of two carriages 100 and 110 and to provide a scatter detector on the same carriage as the source, and a corresponding transmission or forward scatter detector on the oppositely disposed carriage. Alternatively, the imaging apparatus 10 illustrated in FIG. 1 could operate with only one source on one carriage producing penetrating radiation and the oppositely disposed carriage solely detecting radiation produced by that carriage as subject 120 is imaged.

Figure 2A:
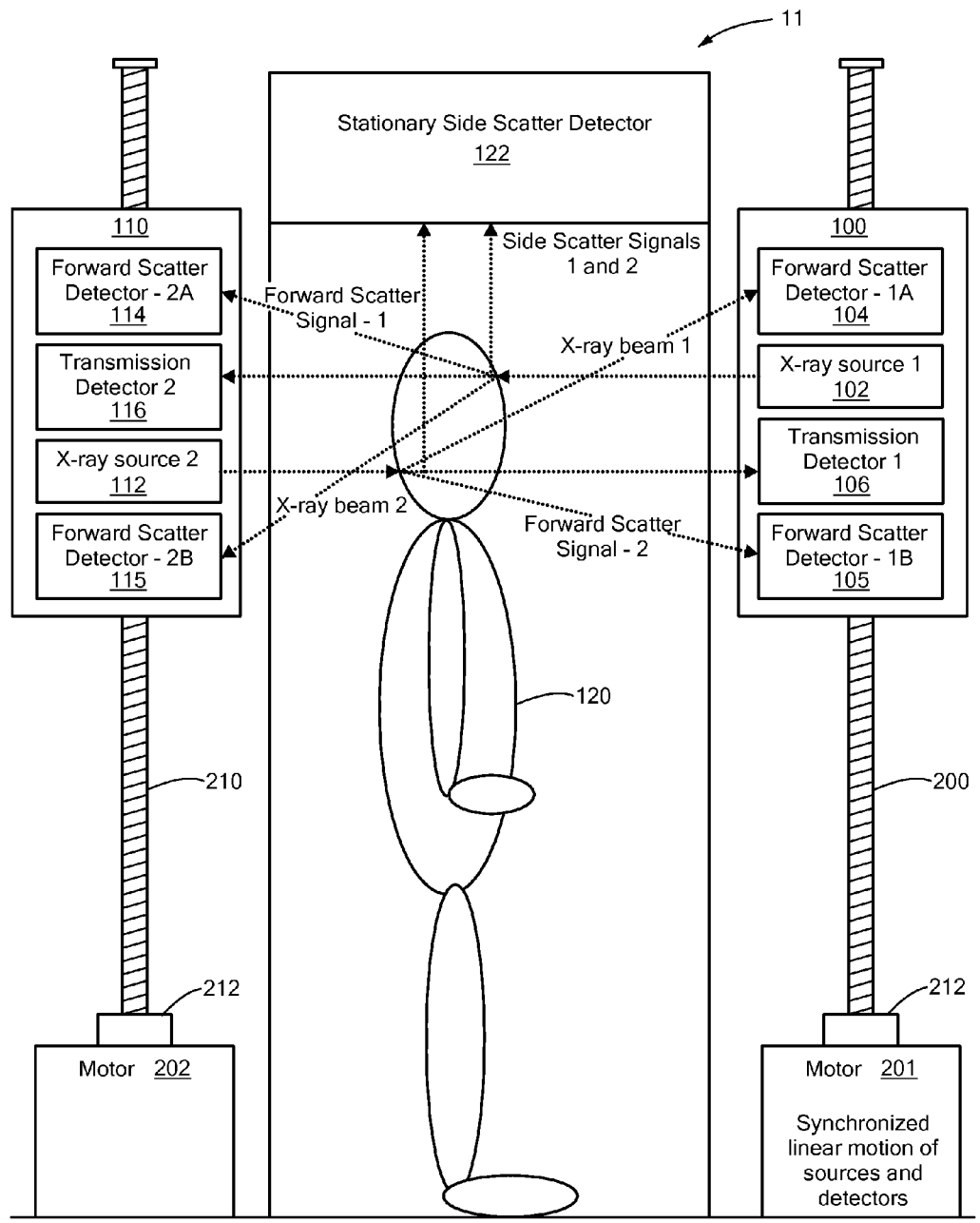
FIGS. 2A and 2B are illustrations of a lead screw type positioner attached to a carriage of the current invention.

FIG. 2A is an illustration of a lead screw type positioner attached to a carriage of the current invention. The imaging apparatus illustrated in FIG. 2A, designated generally by numeral 11 shows lead screws 200 and 210 coupled to carriages 100 and 110 such that as the rotary lead screw motors 201 and 202, here serving as the positioners, are operated simultaneously, carriages 100 and 110 move in a generally vertical direction along the axis of rotation of their respective lead screws. This figure illustrates one type of positioner that may be implemented with carriages 100 and 110 of the current invention to achieve the necessary displacement; however, embodiments of the present invention may incorporate other systems that can be used to achieve displacement of the carriages 100 and 110. These systems may include, but are not limited to, a rack and pinion system, an electro-mechanical system, which may use electro-magnetism propulsion, a hydraulic system, or a pulley system. The invention also contemplates displacing the carriages 100 and 110 by a single positioner that is coupled to the carriages 100 and 110. The positioner may include a single positioner having a mechanical platform coupled to more than one carriage. The positioner may, alternatively or additionally, include a system that allows motion of the carriage or carriages 100 and 110 in a direction or directions other than a vertical direction. Any of the systems described, or any other positioner used, may be commanded by a controller that includes a displacement encoder 212 to provide displacement of the carriages 100 and 110 to a specified position or over a specified displacement. The controller might further command the rate at which the displacement is achieved or any other relevant variables pertaining to carriage movement.

In one embodiment the positioner may be coupled to a displaceable member that subject 120 may be disposed on, as opposed to the positioner being coupled to the carriages 100 and 110. In the embodiment where the positioner is attached to a displaceable member that subject 120 may be disposed on, for example a mechanical platform located between two carriages 100 and 110, the positioner may vary the height of the member in a direction having a vertical component such that the subject 120 or some region of the subject 120 is scanned by the carriages 100 and 110. In this embodiment the same images produced through moving the carriages 100 and 110 in synchronization in a direction having a vertical component are achieved because both embodiments provide for a variation in the relative orientation of the subject 120 with respect to the carriages 100 and 110, while maintaining each carriage at an elevation that does not change with respect to the other carriage.

Figure 2B:
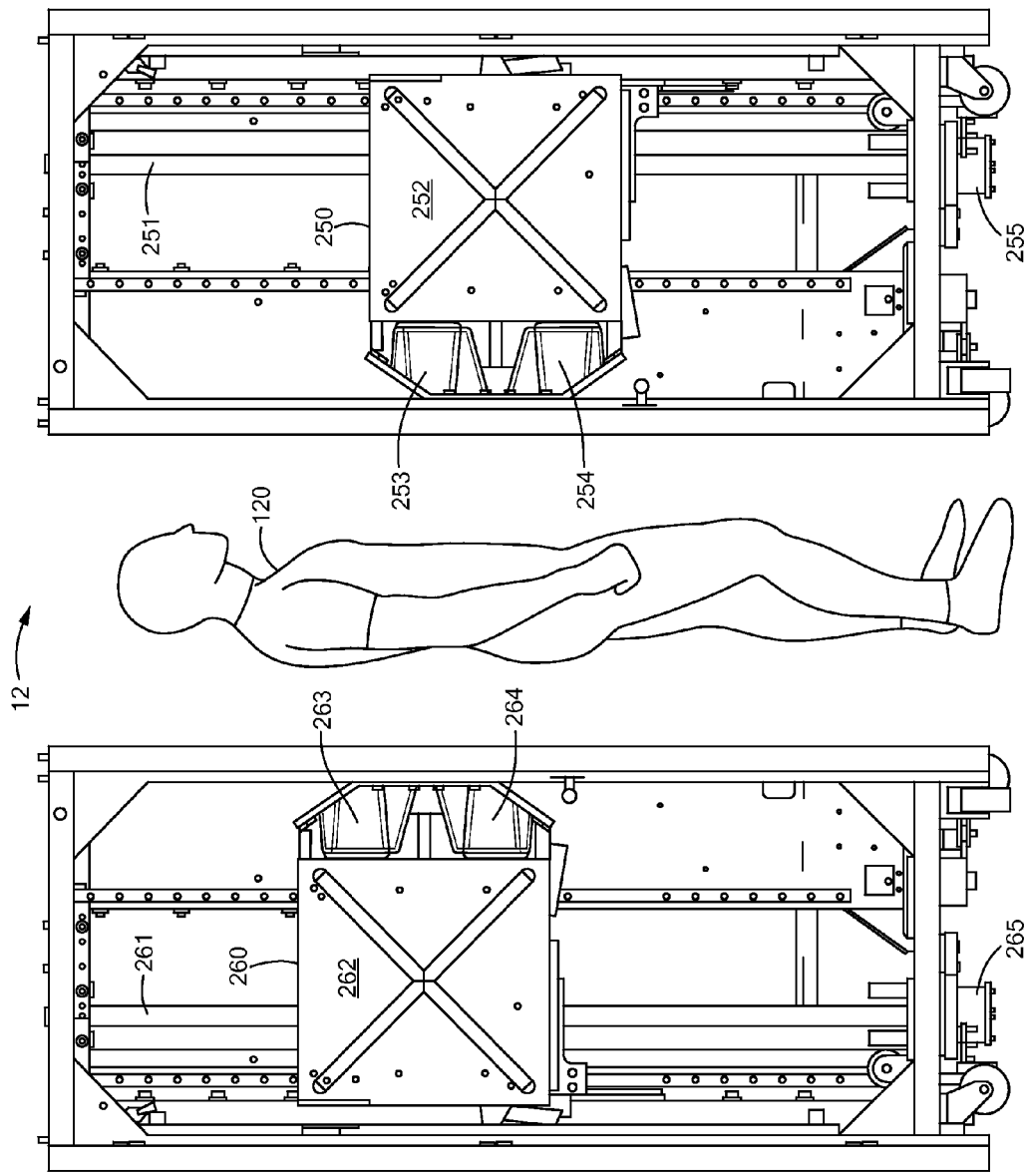

FIG. 2B is a profile view of an embodiment of the present invention used to scan a person who has entered the imaging apparatus. As previously indicated, the sources may be offset from one another such that each source is located at a position that corresponds to the height or elevation of the opposing detector that is configurable for the required type of detection. For example, a detector configurable for transmission detection being located at a vertical height on one carriage that is commensurate with the source located on an oppositely disposed carriage. The imaging apparatus, designated generally by numeral 12 in FIG. 2B shows that offsetting the sources, here source 252 and source 262, may be achieved by offsetting the corresponding carriages, here carriages 250 and 260. For example if the carriages 250 and 260 were similarly configured with the source centrally located and producing a beam of penetrating radiation from a central location on the carriage, each carriage could be coupled to the respective positioner at an elevation whereby one carriage is vertically offset from the other carriage such that the respective source of each carriage is vertically offset with respect to the source of the other carriage. This setup still effectuates the use of configurable detectors as previously discussed. Particularly, during the time interval when source 252 is activated detectors 253 and 254 may be configured to detect backscatter radiation, detector 264 may be configured to detect transmission radiation, and detector 263 may be configured to detect forward scatter radiation. Further, during the time interval when source 262 is activated detectors 263 and 264 may be configured to detect backscatter radiation, detector 253 may be configured to detect transmission radiation, and detector 254 may be configured to detect forward scatter radiation.

FIG. 2B further illustrates lead screws 251 and 261 that provide carriages 250 and 260 with motion in a generally vertical direction as the lead screws are rotated by motors 255 and 265.

Figure 3:
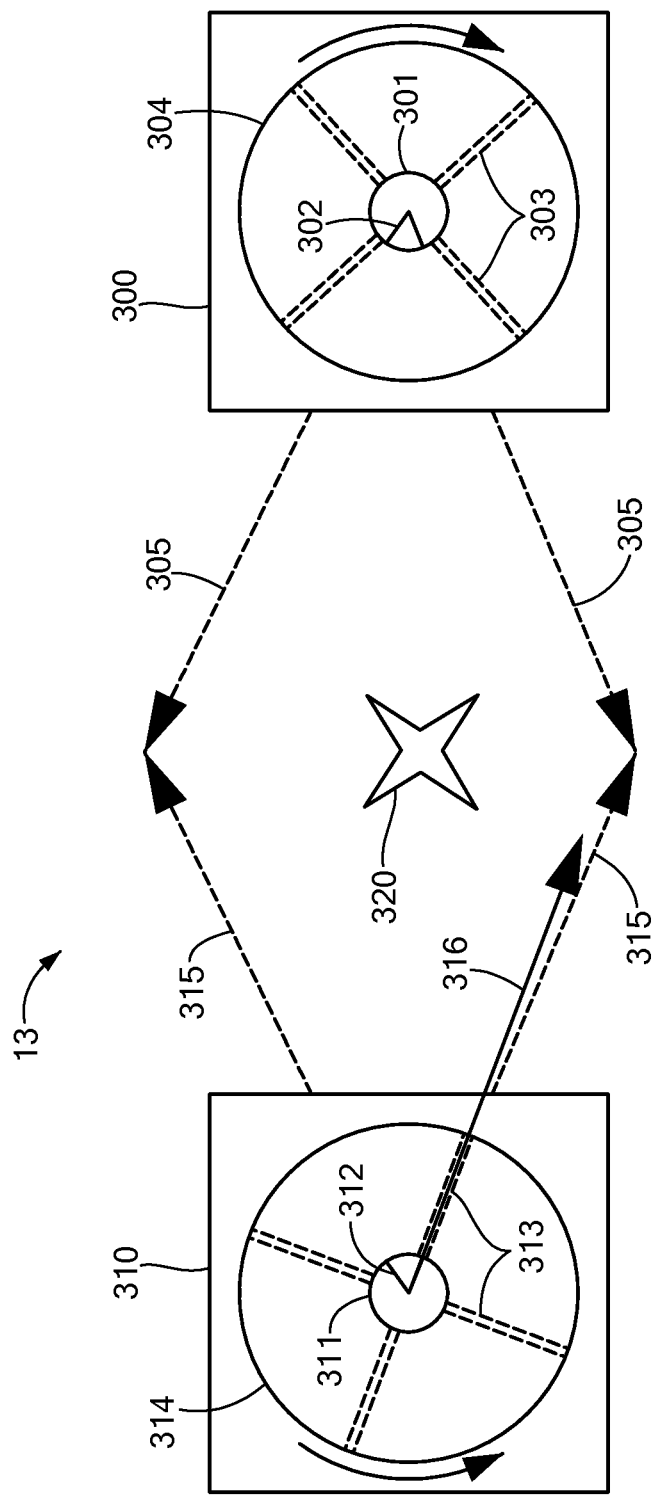
FIG. 3 is a top view of two sources and two chopper wheels configured such that the sources may alternately scan a subject in accordance with an embodiment of the present invention.

FIG. 3 is a top view of two sources with chopper wheels configured such that the sources may alternate producing radiation that is incident on the subject. The imaging apparatus is designated in FIG. 3 by numeral 13. The invention encompasses adapting the sources to produce radiation incident on the subject at distinct time intervals. This may be achieved with a steady state transmitting source or with a pulsed source that transmits radiation during distinct time intervals. In the event that a steady state transmitting source is used, the source may be provided with a chopper wheel that has one-half the normal number of slits, for example. The apparatus will thus be provided with a controller adapted to synchronize the sources irradiation of a subject such that the sources alternate producing radiation incident on the subject during specified time intervals in order to achieve full width scans on both sides of the subject, simultaneous to the carriages being disposed in synchronization in a generally vertical direction, by the positioners or positioner.

In FIG. 3, a first and second carriage 300 and 310 are shown from a top view. The carriages 300 and 310 each illustrate a source 301 and 311 producing penetrating radiation 302 and 312. The penetrating radiation may be produced in a range dictated by the source used, and is not intended to be limited by the illustration. The range of the source is determinative of the range through which the beam of radiation is scanned or swept. This range is illustrated by lines 315 and lines 305. Lines 315 represent the range or window through which a beam produced by source 311 is swept. Lines 305 represent the range or window through which a beam produced by source 301 is swept. The subject is placed between the carriages as illustrated by marker 320 for scanning. The sources produce a beam of radiation that is swept by the chopper wheels 304 and 314. The chopper wheels include openings 303 and 313 that allow the penetrating radiation produced by the respective sources to be emitted through the openings as the wheels move in a generally rotary motion. The rotation of the chopper wheels may include full 360 degree rotations or less. The rotation of the chopper wheels may also include an oscillating rotation or any other motion that allows the radiation to be scanned. The wheels are designed to effectively shield the radiation emitted from the source on an interval during which any of the openings 303 and 313 are not in front of the direction of radiation emission from their respective sources. As such the wheels may be constructed of lead or any other suitable material that effectively shields the radiation produced by the source used. As shown in the figure, beam 316 begins sweeping through range 315 simultaneous to chopper wheel 304 shielding radiation 302 produced by source 301. The beams will continue to alternate being swept as the carriages are moved in a vertical direction, into or out of the plane of the page, in order to achieve a complete scan of the subject. Alternative configurations may be provided that allow different interleaved irradiation schemes.

Figure 4:
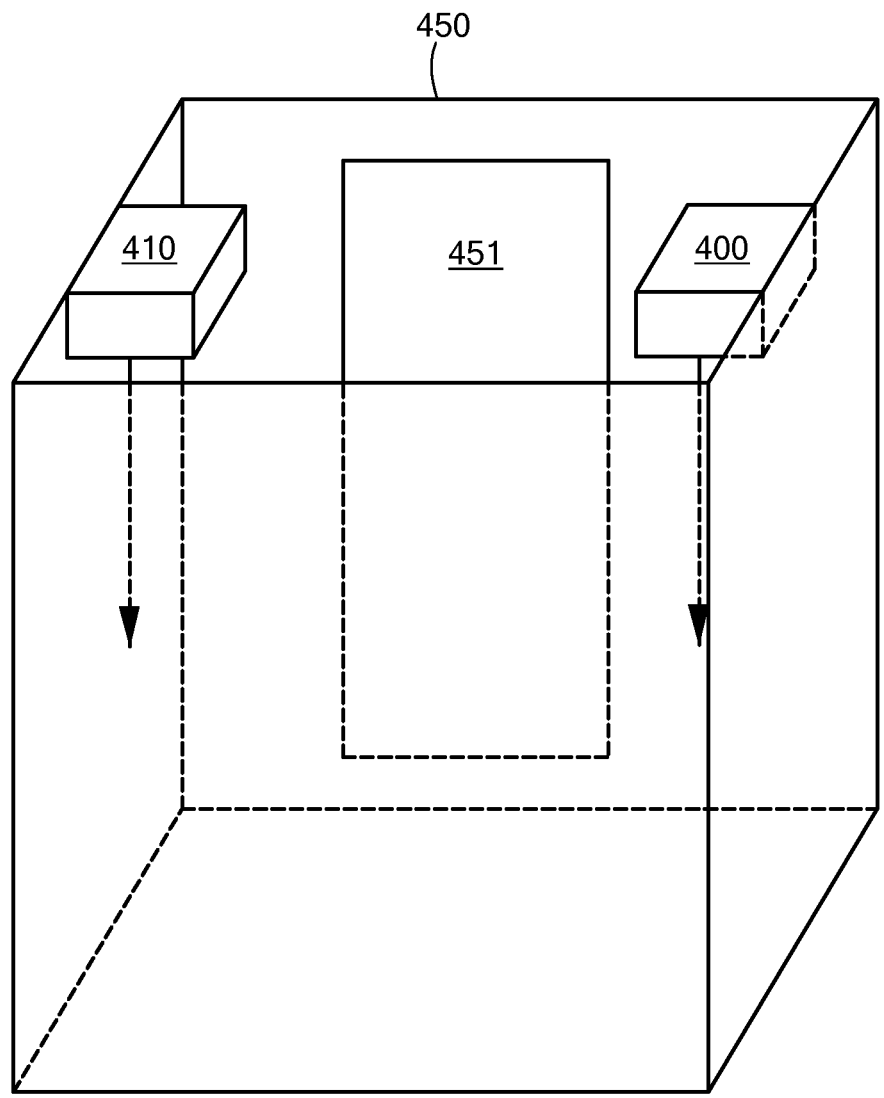
FIG. 4 illustrates an inspection system provided within an enclosure, in accordance with certain embodiments of the present invention.

FIG. 4 is an illustration of the inspection system provided within an enclosure for containing the carriages and the at least one positioner during the course of operation. The enclosure 450 may include a portal 124 (shown in FIG. 1) that a subject may enter for scanning. The enclosure 450 may be provided in a mobile form. The enclosure 450 illustrated is provided with carriages 400 and 410 that may contain the desired detector source combination required for the specific scanning application. These carriages 400 and 410 are displaced in a generally vertical direction. The enclosure 450 may also include a stationary scatter detection system 451. The enclosure 450 may include stationary detectors located on the top, bottom, or any other sides of the container. The information obtained from each of these detectors may be viewed or processed individually or the information may be processed and combined with the information from another detector or detectors, including the detectors located on a carriage in order to obtain greater details about a concealed object of interest located on a scanned subject. The enclosure 450 may also include onsite inspection controls and an analysis system or the enclosure 450 may be adapted for use with a remote analysis system. The enclosure 450 may provide for environmental control so that the internal temperature, humidity, air pressure, microbial or contaminant content, or other environmental factor may be regulated. The 450 enclosure may seal an interior portion of the enclosure from the surrounding outside environment.

Some embodiments of the present invention may relate to methods and systems for inspecting objects by means of penetrating radiation that use multiple x-ray sources, which may be individually activated, as described in U.S. Patent Application Publication No. 2007/0258562 (issued as U.S. Pat. No. 7,505,562), hereby incorporated by reference herein in its entirety.

X-ray sources may be based on field-emission cathodes, offering advantages in both spatial and temporal resolution when compared with thermionic sources. Because field emission of electrons is produced by a high electric field, no heating is necessary, whence such electron emitters are commonly referred to as cold cathodes. The electron beams emitted by such devices may have low divergence and thus provide ease of focusing. Moreover, the virtually instantaneous response of the source offers time gating capabilities comparable with the time resolution of the control circuit, and may be as fast as nanoseconds, using current technology.

Zhang et al., *A Multi-beam X-ray Imaging System Based on Carbon Nanotube Field Emitters*, in *Medical Imaging* 2006, (Proceedings of SPIE, Vol. 6142, Mar. 2, 2006), reported the fabrication, by Xintek, Inc. of Research Triangle Park, N.C., of a linear array of 5 X-ray sources, each with a focal spot between 200 and 300 μm, based on the use of carbon nanotube (CNT) electrodes. Electron currents in the range of 0.1-1 mA were reported at an accelerating voltage of 40-60 kVp. The lifetime of the cold cathode was estimated to exceed 2000 hours. For an accelerating voltage of 200 kV, a beam current of 13 mA has been measured. The aforesaid Zhang et al. paper is incorporated herein by reference. Devices with 1000 pixels per meter and pulse repetition rates on 10 MHz can be envisioned with technology within the current state of the art.

The use of CNT cold cathodes in the context of an x-ray source is also described by Cheng et al., *Dynamic radiography using a carbon-nanotube-based field-emission X-ray source*, Rev. Sci. Instruments 75, p. 3264 (2004), while the use of CNT cold cathode source arrays in a scanning context is described by Zhang et al., *Stationary scanning x-ray source based on carbon nanotube field emitters*, Appl. Phys. Lett 86., p. 184104 (2005), both of which articles are incorporated herein by reference.

Moreover, the use of CNT cold cathode source arrays in tomography is discussed by Zhang et al., *A nanotube-based field emission x-ray source for microcomputed tomography*, Rev. Sci. Instruments 76, p. 94301 (2005), which is also incorporated herein by reference.

Discrete cold cathode sources may advantageously provide for electronically turning on the sources, and with low latency (on the nanosecond scale), in a sequential manner, thereby forming pencil beams, as often practiced in the x-ray imaging arts, or, alternatively, selecting a pattern of sources at a given time to form coded beams. The development of CNTs has allowed important technical challenges related to current stability and cathode life time to be overcome.

The general operation of a cold cathode x-ray source, designated generally, in FIG. 5, by numeral 1010, is well understood in the art and is described with reference to FIG. 5. The cold cathode arrangement advantageously allows for a high degree of control. The voltage between gate 1012 and cathode 1014, governed by control circuit 1013, controls the current of electrons 1015, while the voltage between cathode 1014 and anode 1016, which also serves as the X-ray target, controls the electron energy impinging on the anode 1016, and the voltage applied on the focusing electrode 1018 determines the electron beam spot size.

Figure 5:
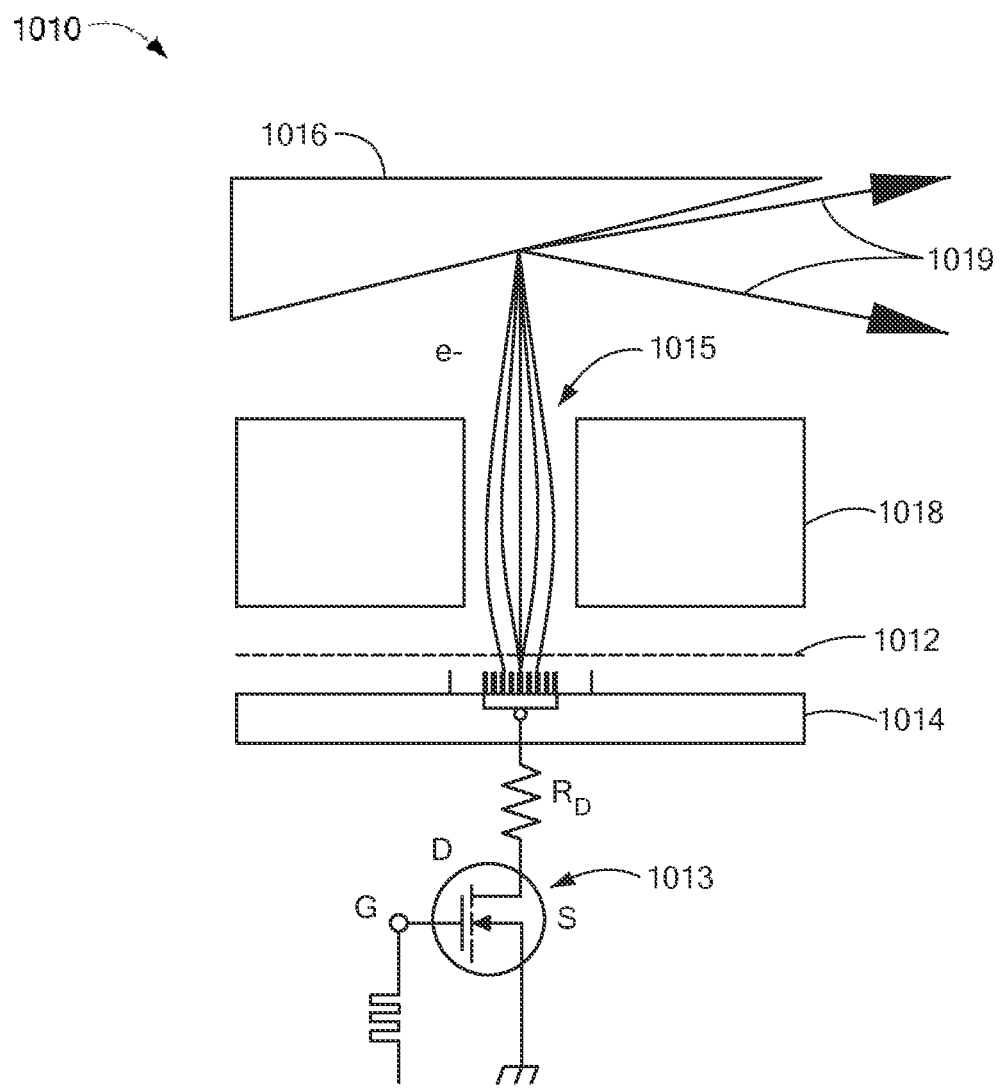
FIG. 5 is a schematic depiction of a prior art x-ray source based on electron field emission.

While FIG. 5 depicts an assembly in which the x-rays 1019 are generated via a reflection target, a transmission target may also be employed within the scope of the present invention.

Application of discrete x-ray sources for x-ray imaging, in accordance with the present invention, varies with the dimensionality of the x-ray source array (one-, two-, or three-dimensional), the scanning mode (raster or pattern), the dynamic use of different or varying energies, and the use of time gating.

Figure 6:
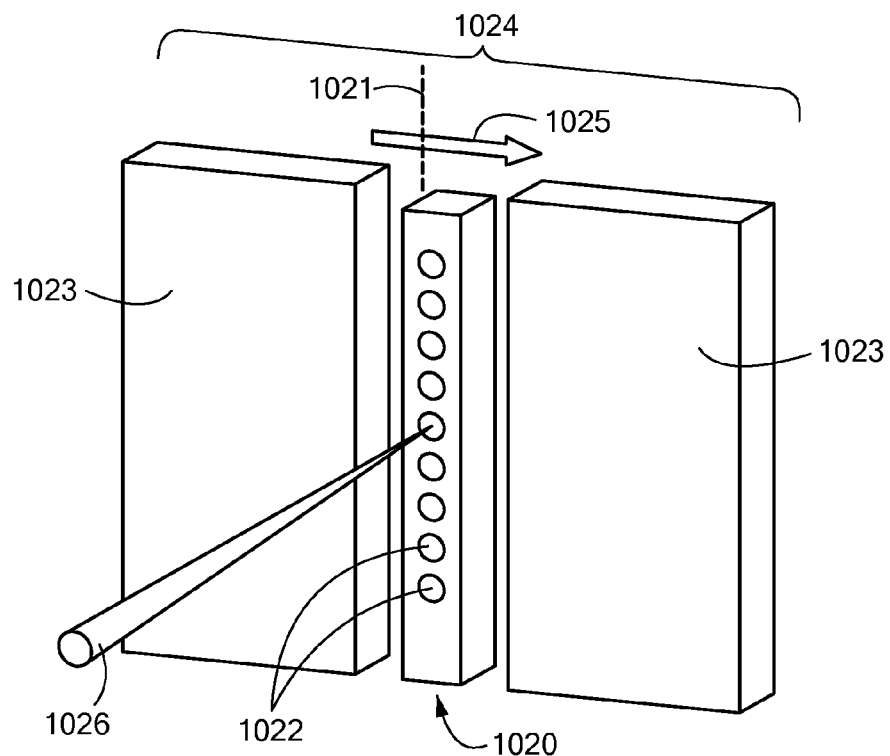
FIG. 6 shows the use of a single-dimensional array of discrete sources in a backscatter imaging application, in accordance with an embodiment of the present invention.

An embodiment of the invention is described with reference to FIG. 6. A one-dimensional array 1020 of x-ray sources 1022 is disposed with backscatter detectors 1023 on one or more sides of its longitudinal (typically vertical) axis 1021. The entire device 1024 can translate in a transverse direction 1025, typically horizontally, so as to create an image on a line-by-line basis. Alternatively, array 1020 may rotate about longitudinal (typically vertical) axis 1021 such that x-ray beam 1026 sweeps in a transverse direction (again, typically horizontally), thereby creating a line-by-line image, but without the entire device moving. An image line is created by raster scanning the sources vertically by turning on one source 1022 at a time in rapid succession.

Figure 7:
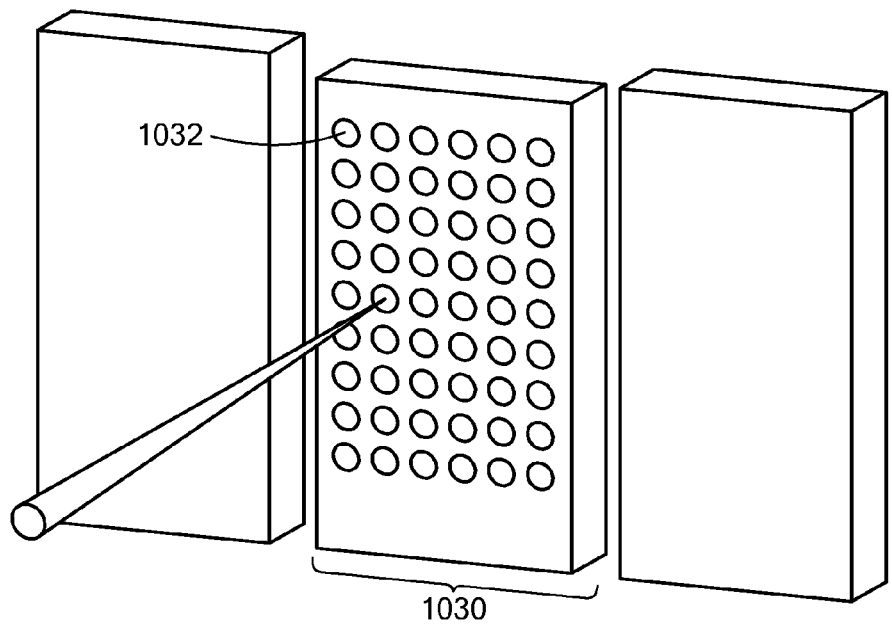
FIG. 7 shows the use of a two-dimensional array of discrete sources in a backscatter imaging application, in accordance with an embodiment of the present invention.

Referring now to FIG. 7, a two-dimensional source array 1030 may have no mechanically moving parts and allow coverage of a predefined solid angle (determined by the total number of sources 1032 and their divergence) in a very short time. It can use a raster scan mechanism similar to a CRT or pattern beams (Hadamard or other coding mechanism).

Figure 8:
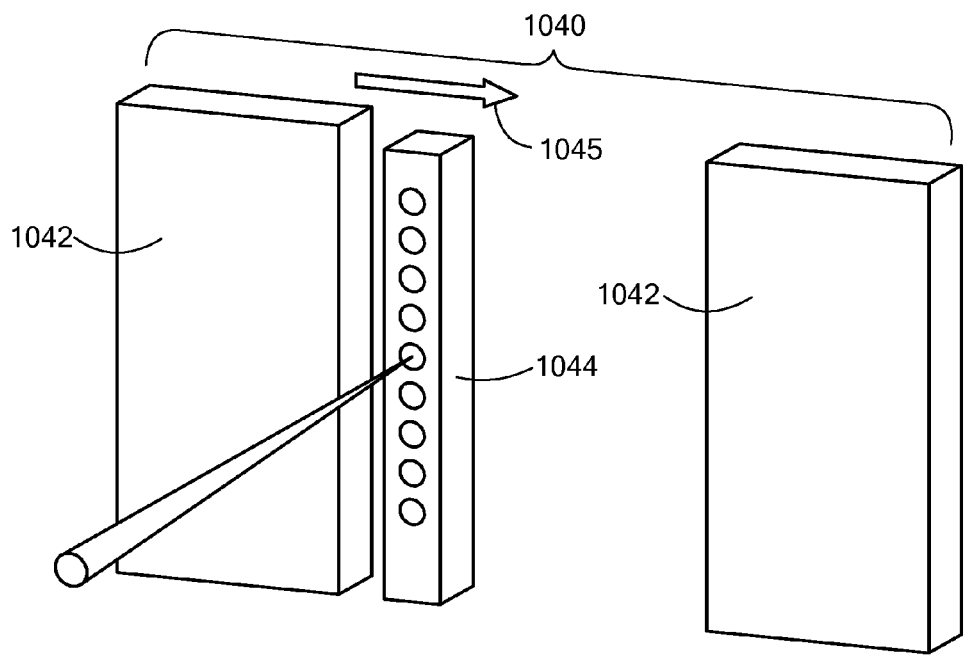
FIG. 8 shows the use of a single-dimensional array of discrete sources and a fixed set of backscatter detectors in a backscatter imaging application, in accordance with an embodiment of the present invention.

In accordance with further embodiments of the present invention, a system with controlled velocity, designated generally by numeral 1040, is described with reference to FIG. 8. One or more backscatter detectors 1042 are fixed, but the source array 1044 is translated with a constant speed back and forth in direction 1045 adjacent to, or between, backscatter detectors 1042. Such system may also be employed in an interlaced mode, described below.

Figure 9:
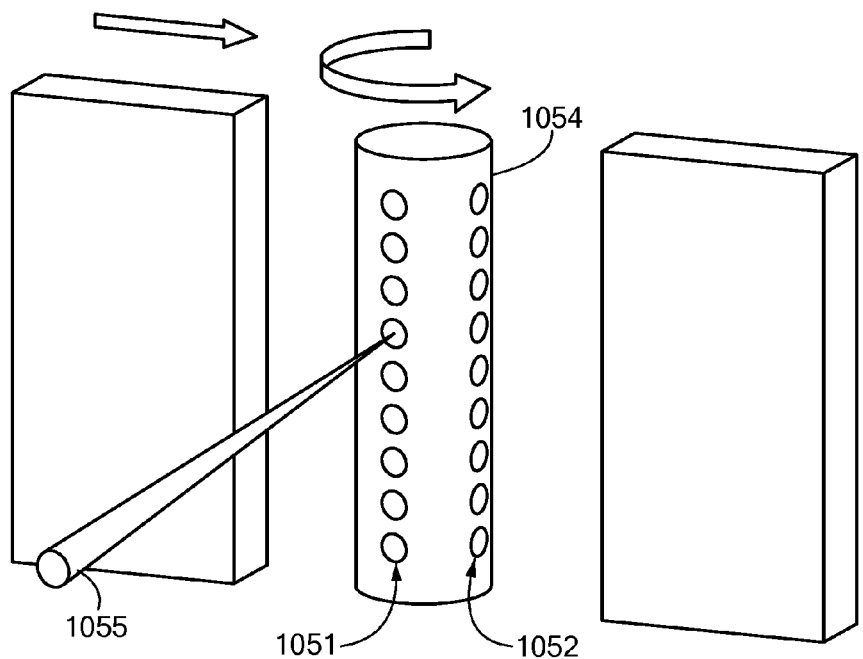
FIG. 9 shows an image generation apparatus in which multiple one-dimensional source arrays are mounted on a single cylinder, in accordance with an embodiment of the present invention.

Further versatility may be achieved using a related embodiment such as that shown in FIG. 9 where two or more one-dimensional x-ray source arrays 1051, 1052, are mounted on a cylinder 1054. Because the arrays can be turned on and off electronically with high speed, only the array generating an x-ray beam 1055 that is illuminating a target (not shown) is turned on, and the other arrays are off, hence there is no need to shield one array from another. The versatility of this model resides in its natural ability to incorporate the interlaced mode, as now described, and to continuously accumulate an image. Alternatively two cylinders could be provided to produce radiation incident on two sides of a subject. The sources in each array may be provided with a controller for independent activation of the sources.

Interlacing can be useful in cases where, due to technical limitations or by design, the minimum distance between two sources is 1 cm, but the required resolution for a specific applications demands sources placed 4 mm apart. On a cylinder, three one-dimensional arrays are placed at 120 degrees one from another and shifted vertically by 3.33 mm. Each array will scan lines 1 cm apart, but because of the vertical shift, the resulting image for a complete rotation of the cylinder will have a resolution of 3.33 mm. This mode of operation is referred to as "interlaced mode." For the system depicted in FIG. 8, interlaced imaging may be provided via vertical translation of the array for each horizontal pass.

In accordance with further embodiments of the present invention, carbon nanotube x-ray sources configured in a linear or two-dimensional are triggered sequentially as described above. Other discrete x-ray sources that currently exist or that may be developed in the future may also be employed in a substantially similar manner, and are within the scope of the present invention as described herein and as claimed in any appended claims.

The use of x-ray source arrays of this type for this application may be particularly advantageous for the following reasons:

- The x-ray source can be very compact, especially in the dimension along the line of x-ray emission.
- Use of a linear array of x-ray beams advantageously reduces image distortion associated with single point sources.
- This approach to generating x-rays provides flexibility in image acquisition, geometry and footprint that is far superior to current single point x-ray source-based systems.
- By using sequential triggering of the linear array of x-ray sources, a backscatter image can be acquired without cross-talk between sources.
- This invention, when applied in a configuration that simultaneously captures two or more views of the person being scanned, advantageously enhances the throughput of inspected subjects.

Figure 10A:
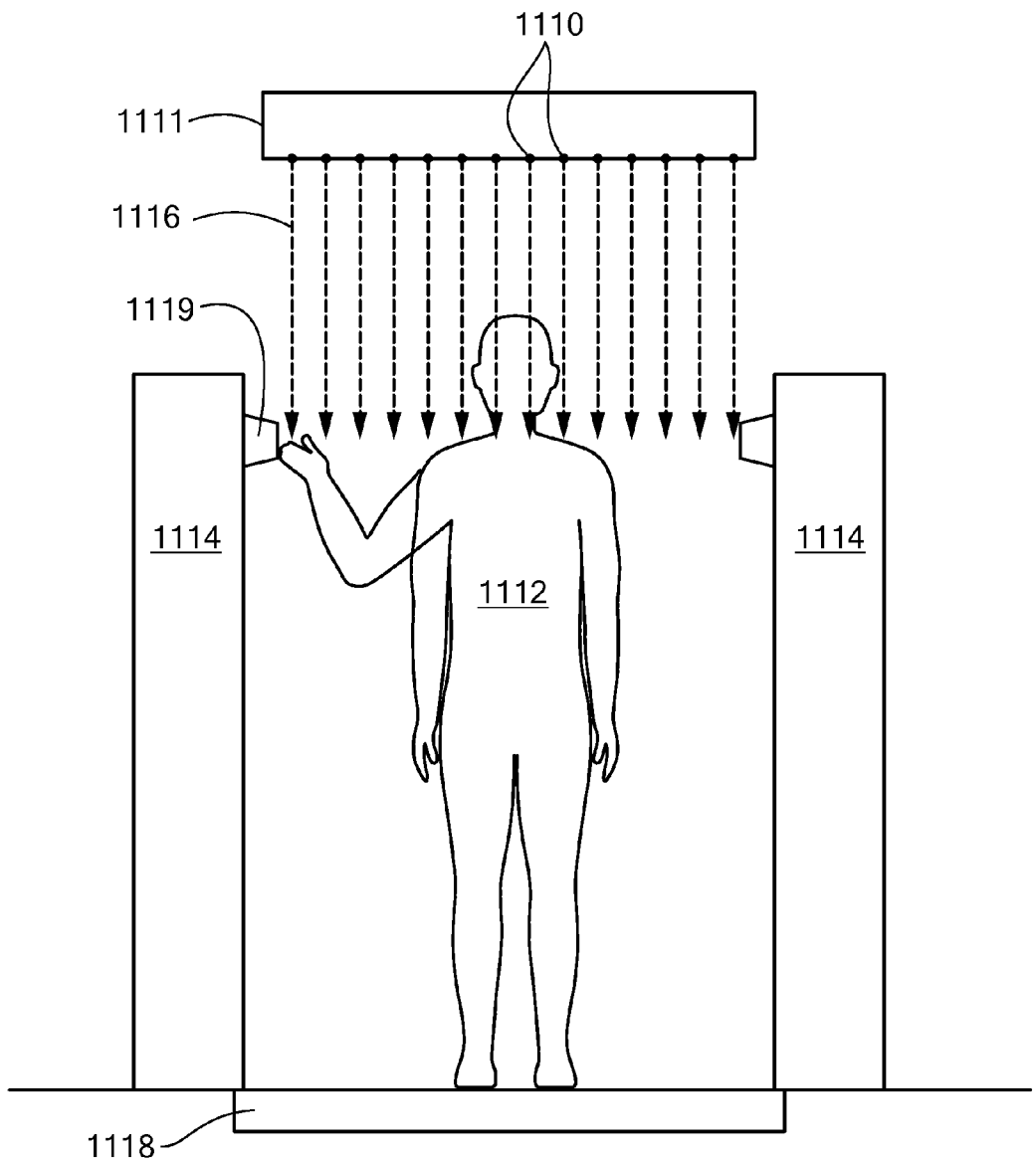
FIG. 10A shows a front view of an embodiment of the present invention in which x-rays are emitted from above.

Another embodiment of the invention is now described with reference to FIG. 10A. Sets of carbon nanotube x-ray sources 1110 configured as linear arrays 1111, or as a two-dimensional array, are placed above (as shown) or at the sides of, a person 1112 being scanned. It is to be understood that a person is shown as a representative object of inspection, but that the apparatus and methods taught herein are of valuable applicability to any object, whether animate or inanimate.

Figure 10B:
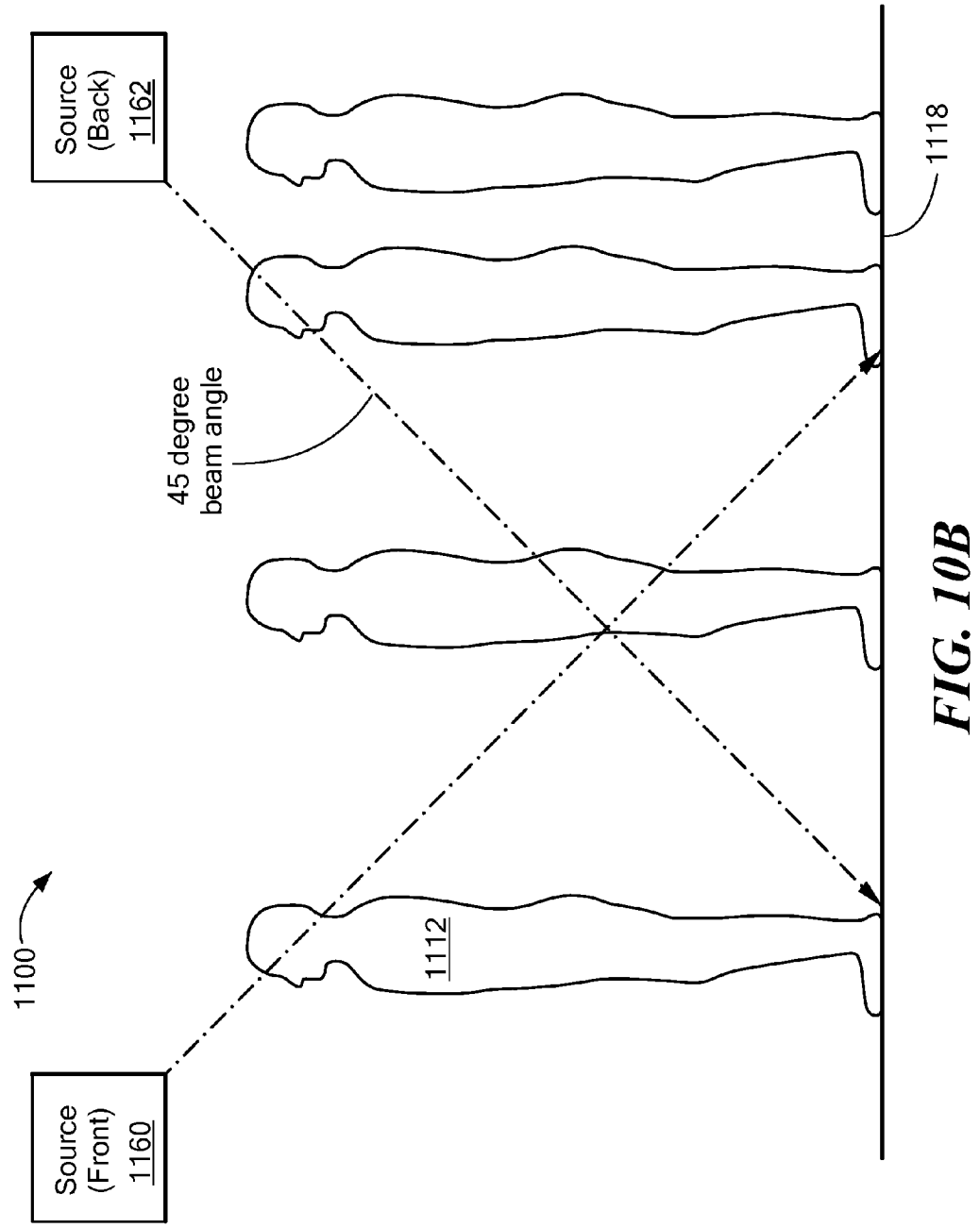
FIG. 10B shows a schematic side view of an embodiment of the present invention, depicting a person at successive positions traversing a plurality of x-ray beams emitted from above.

Scatter detectors 1114, which may be backscatter or side-scatter detectors, for example, are positioned to capture scattered x-rays. The person being scanned walks through the x-ray beams 1116 or is transported through by means such as a conveyor 1118 or people mover. A hand-hold 1119 may also be provided. Separate sources 1110 may be activated sequentially to provide spatial resolution in accordance with known algorithms. FIG. 10B depicts subject 1112 in successive positions traversing an inspection station that is designated generally by numeral 1100. Inspection station 1100 has a front source 1160 and a back source 1162, each of which may contain linear arrays, such as source 1111 depicted in FIG. 10A, each of which is comprised of multiple discrete x-ray sources disposed along an axis transverse to the page. Subject 1112 either walks, or is conveyed by conveyor 1118, in such a manner as to have different parts of his/her person scanned by respective sources 1160 and 1162 during the course of traversing the inspection station.

Figure 11A:
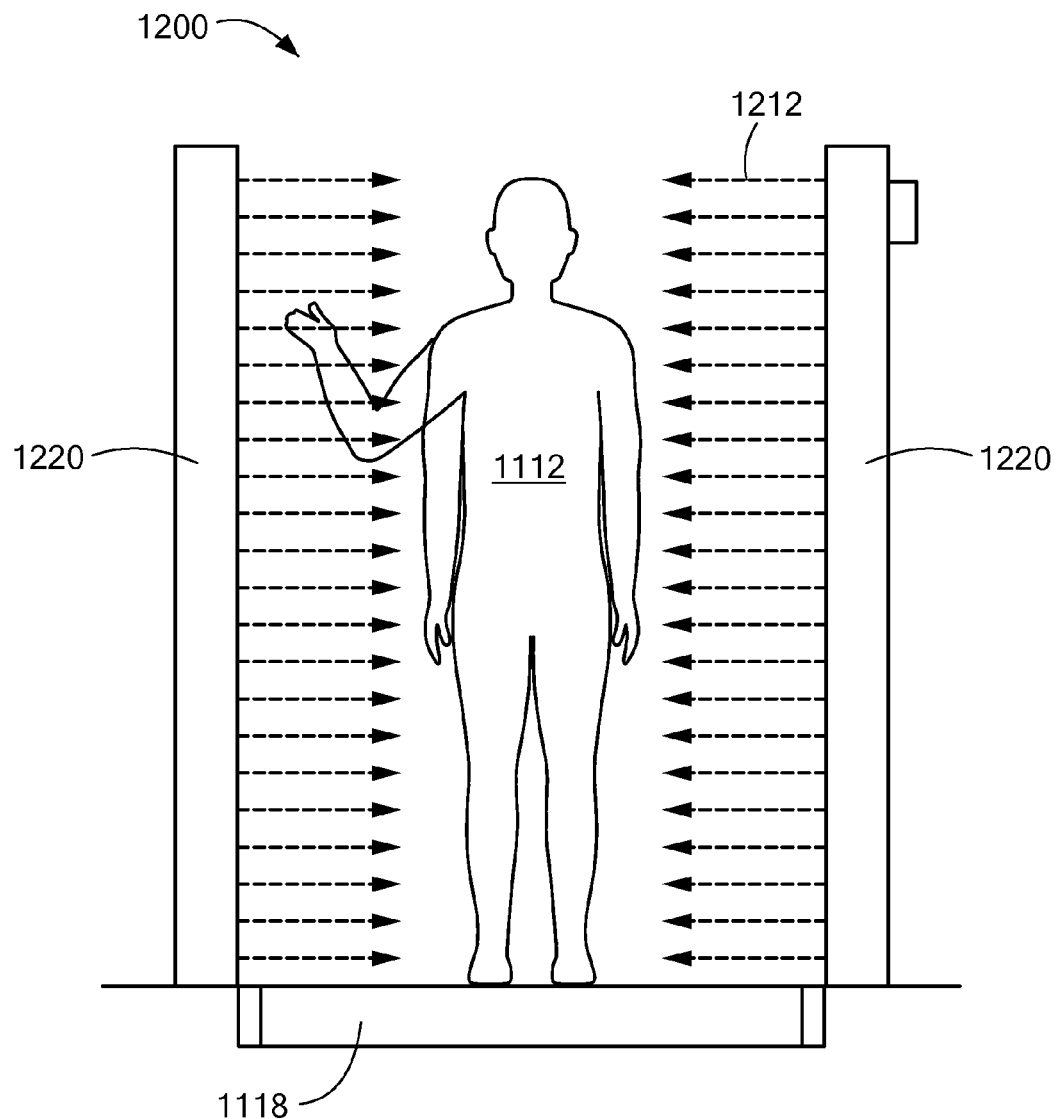
FIG. 11A shows a front view of an embodiment of the present invention in which x-rays are emitted from opposing sides.
Figure 11B:
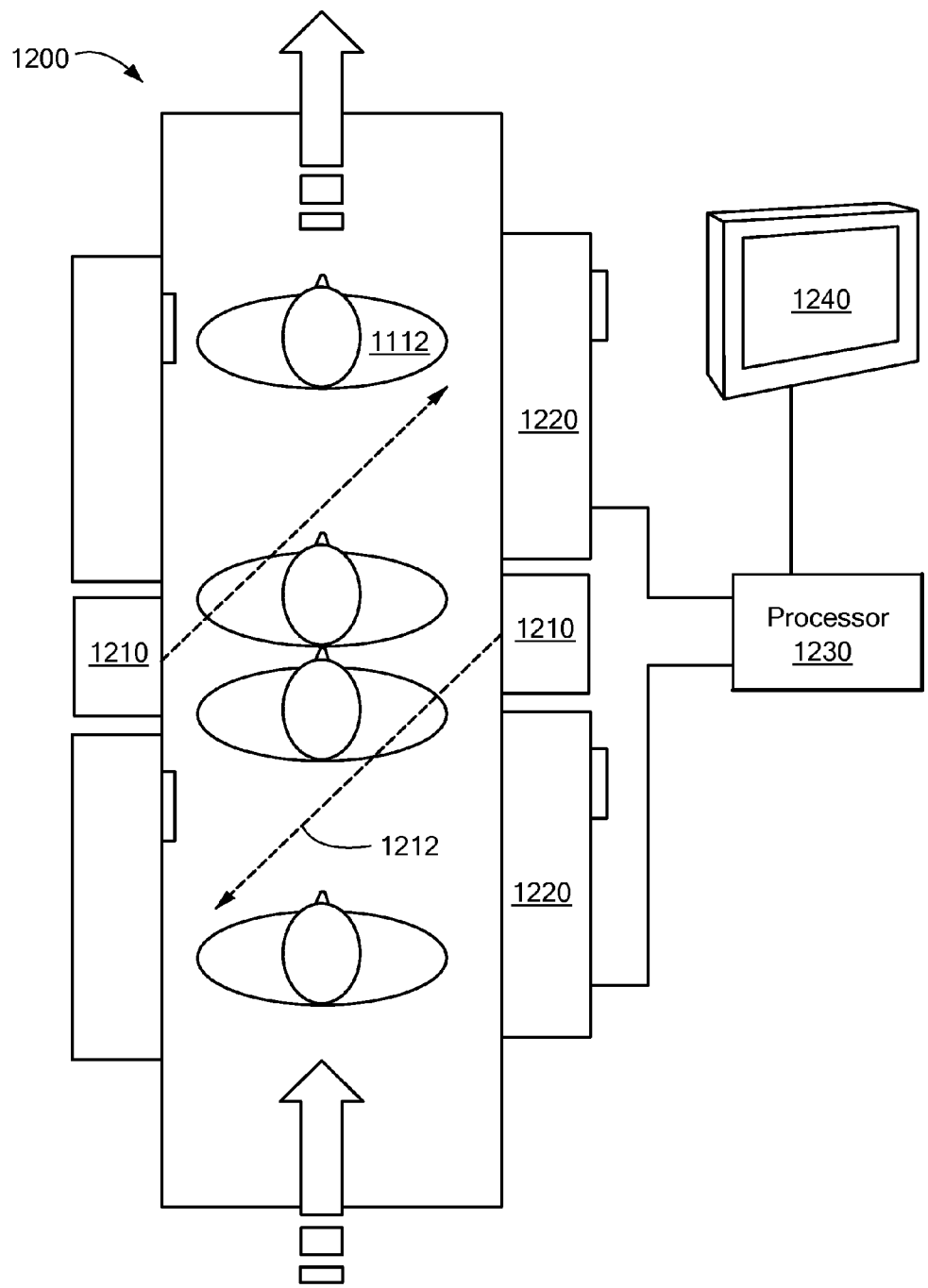
FIG. 11B shows a schematic side view of an embodiment of the present invention, depicting a person at successive positions traversing a plurality of x-ray beams emitted from above.

Yet a further embodiment of the present invention is shown in FIGS. 11A and 11B, in a configuration approaching that of metal detectors in current use. As shown in the top view of FIG. 11B, x-ray source arrays 1210 emit x-rays 1212, viewed most clearly in the front view of FIG. 11A. Array 1210 may be provided as a vertically disposed array. Each source in each array may be activated independent of the other sources in the array in accordance with an embodiment of the present invention. X-rays 1212 impinge upon subject 1112 as he/she traverses the inspection station, designated generally by numeral 1200. Radiation scattered by subject 1112 or by objects carried or worn on the subject's person is detected by scatter detectors 1220. Scatter detectors 1220 generate scatter signals on the basis of the penetrating radiation they detect, and the scatter signals are processed by processor 1230 to detect and identify threat materials and objects in accordance with known algorithms, or, otherwise, to display a suitably processed image of the inspected subject at display monitor 1240. In either case, an image is generated, with the term "image," as used herein and in any appended claims, signifying an ordered array of values corresponding to spatially distinct elements of the inspected object. Since the geometry minimizes distortion and shadowing of the image data, automated detection techniques that rely on shape recognition greatly benefit from the reduced image distortion and shadowing. These advantages may also be applied to conventional transmission and backscatter baggage systems.

Figure 14:
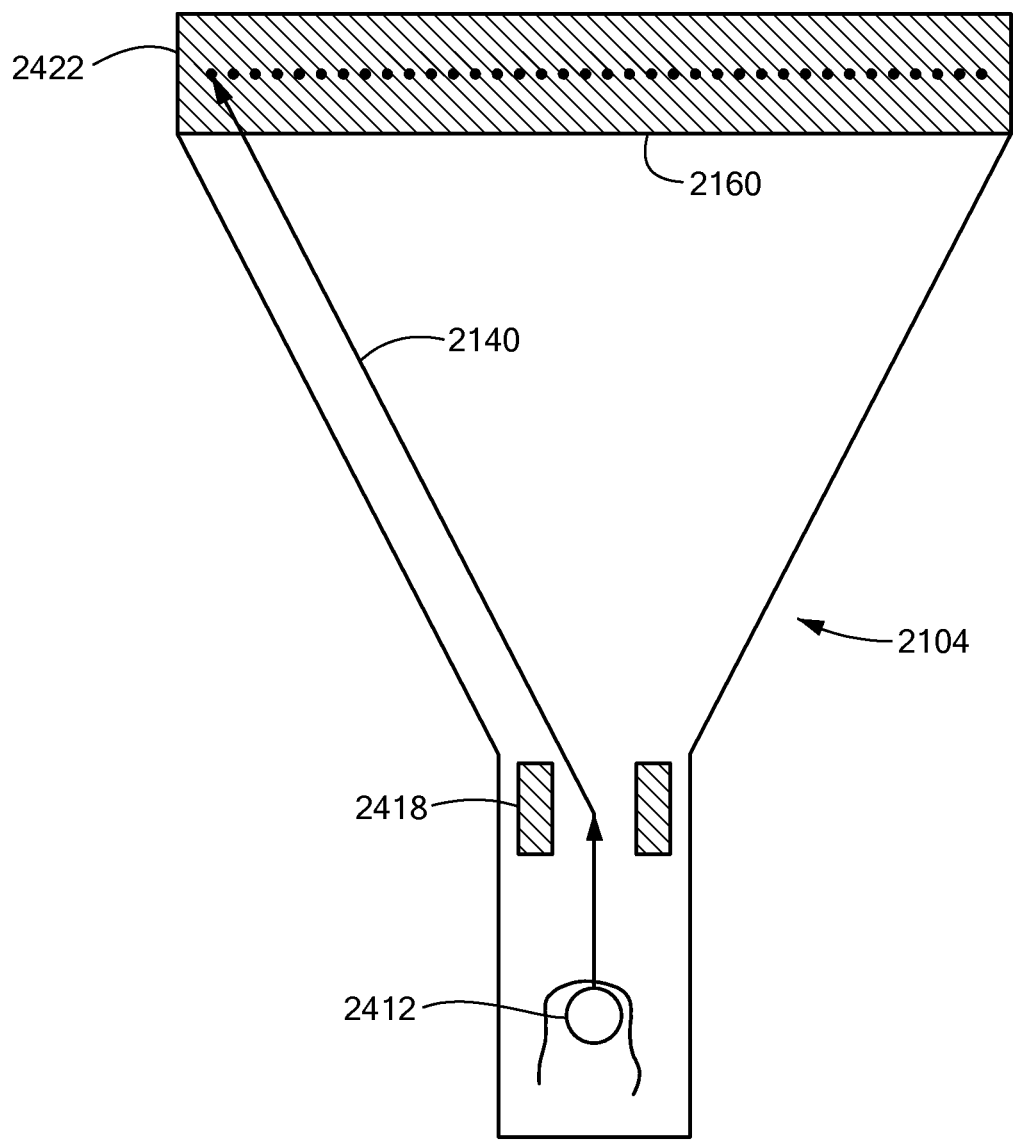
FIG. 14 shows a prior art backscatter system employing an electromagnetic scanner of a sort employed in various embodiments of the present invention.

Alternatively, electromagnetic scanners may be employed, such as scanner 2104 (shown in FIG. 14) and those described in U.S. Pat. No. 6,421,420, issued Jul. 23, 2002 and entitled "Method and Apparatus for Generating Sequential Beams of Penetrating Radiation," which is incorporated herein by reference. A source 2412 supplies a beam of charged particles 2140 that are accelerated to a surface of a target 2160. Electromagnetic beam director 2418 can be any electromagnetic beam directing arrangement such as magnetic or electrostatic yokes. Penetrating electromagnetic radiation is emitted by target 2160 and pass through a collimator 2422 disposed a specified distance from the target, thus producing sequential parallel beams of radiation.

Figure 12:
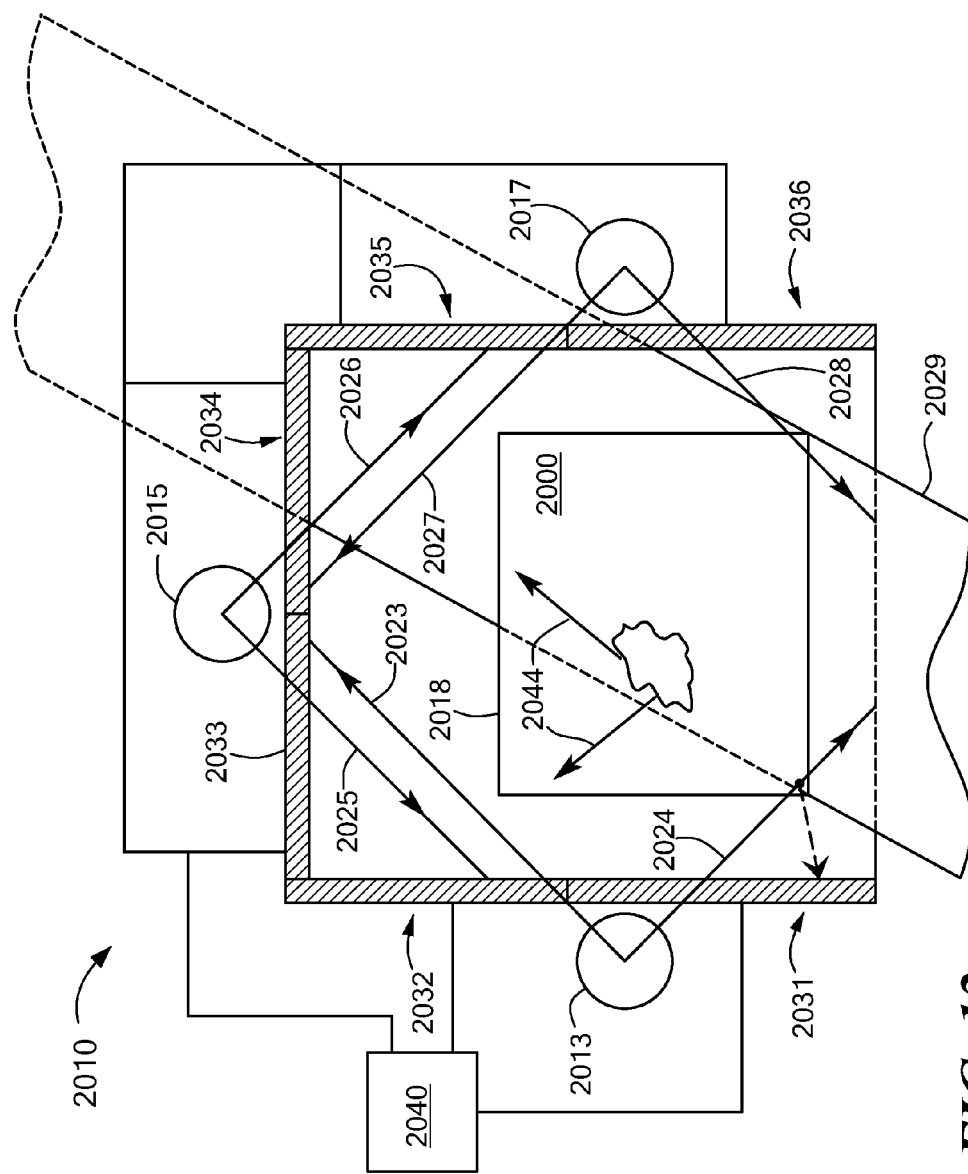
FIG. 12 shows a schematic cross sectional view of an x-ray inspection system that uses multiple backscatter imaging systems in accordance with embodiments of the present invention.

In cases where flying-spot systems are realized by mechanical means such as rotating hoops and chopper wheels, these aforesaid criteria may be met by synchronization of the motion of the mechanical chopper elements, biased by phase offsets. A system capable of such operation is demonstrated in U.S. Pat. No. 7,400,701, hereby incorporated by reference herein in its entirety. Thus, for example, as shown in FIG. 12, where collimators are rotated to define the path of emergent x-ray beam 2023, close-loop motion controller systems known in the art may be employed to drive the rotation of the collimators. The duty cycle is controlled by setting the fan aperture (the total sweep angle of a beam, i.e., the angle between extremal beams 2023 and 2024 of a single source), equal to $2\pi$ times the duty cycle. In systems where the emitted radiation can be controlled electronically, any desired sequence of irradiation or range of sweep may be set, without limitation, entirely by electronic or software control.

By virtue of temporal sequencing which reduces or eliminates cross-talk, sources may be placed in greater proximity than otherwise possible. In particular, sources 2013, 2015 and 2017 may be disposed in a single plane, which advantageously permits virtually simultaneous on/off control of the x-rays regardless of the speed with which the object is passing by the imagers.

The system described may advantageously provide for an image to be derived from the perspective of each successive source 2013, 2015 and 2017, which emit beams 2023-2028. FIG. 12 shows an exemplary three-view system 2010, with beams 2023, 2025, 2027, etc. each sweeping trajectories that are coplanar.

The beams from each imager sweep in sequence, such that no more than one imager is emitting radiation at a time. Thus, source (or 'imager') 2013 sweeps its beam first. Radiation scattered from an object 2018 in a container 2000, as represented by rays 2044, is received by all of the detectors 2031-2036 and transmitted to a processor 2040 to obtain images of the object 2018. The container 2000 may be conveyed through the system by an optional mechanized conveyor 2029. The signals from each of the detectors are acquired as separate channels by an acquisition system. This process is repeated for each of the three sources, creating "slices" of the object as it moves by.

Figure 13:
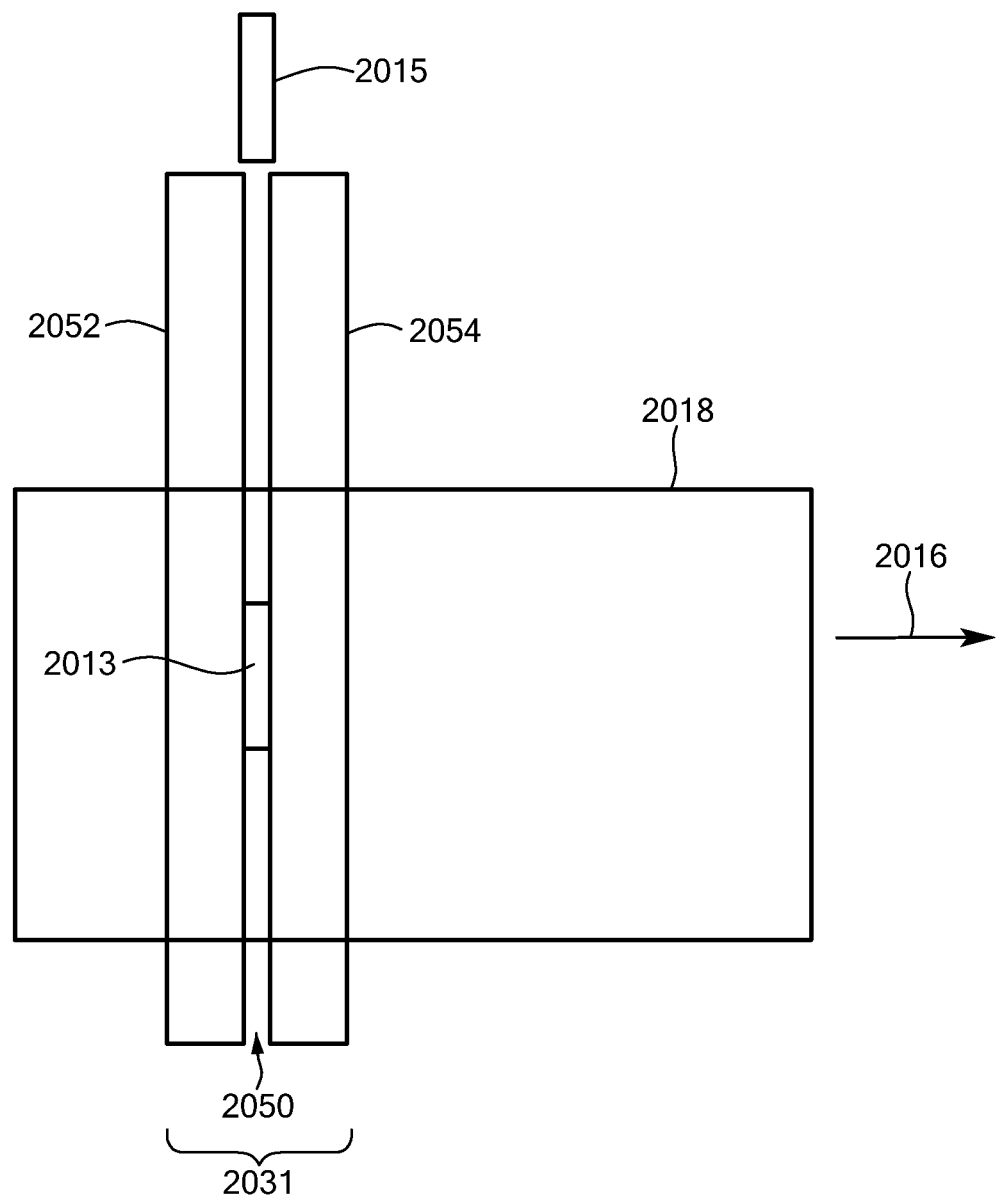
FIG. 13 shows a side view of the x-ray inspection system embodiments of FIG. 12.

Referring now to FIG. 13, a side view is shown of the arrangement of FIG. 13, with elements designated by corresponding numbers. A slot 2050 is shown through which the beam of source 2013 passes through segments 2052 and 2054 of detector 2031 as object 2018 is scanned while container 2000 moves in a lateral direction 2016.

The signals from the detectors can be selectively used to reconstruct an image of the object 2018. Since scattered photons 2044 detected by detectors 2033 and 2034 from source 2013 are as useful as scattered photons from source 2017, these same detectors can be shared among all sources, and result in improved scatter collection with efficient use of the detector hardware.

Embodiments of this invention, furthermore, may advantageously allow multi-view Flying-Spot X-ray Scatter imaging to be practiced in a smaller operational footprint by eliminating cross talk, and by allowing closer positioning of the individual imagers for each view. The close positioning of these imagers (where an "imager" refers to a source, at least one detector, and associated electronics and signal processing) may also allow sharing of scatter detectors between, or among, imagers, allowing more scatter collection for improved image quality, with efficient use of detector hardware.

In applications where scanning of selective regions of the object is desired, co-planar positioning of the imagers allows simultaneous on/off control of the x-rays regardless of the speed with which the object is passing by the imagers. This greatly simplifies the design of the control of x-ray emissions from each imager in the multi-view inspection system, thus individual sequencing of x-ray emissions need not be performed as is typically practiced in systems in which emission is not co-planar.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. An imaging apparatus for detecting a concealed object carried on a stationary human body comprising:
 a first module, further comprising a first X-ray source for producing a first pencil beam of X-rays directed toward said human body
 and a first detector assembly providing a signal representative of the intensity of the X-rays scattered from said human body as a result of being scanned by the first X-ray source,
 said first detector assembly being disposed on a same side of said human body as said first X-ray source and having an active area for receiving a portion of said scattered X-rays from said human body as a result of being scanned by said first X-ray source and a portion of transmitted X-rays from a second module; and the second module, further comprising a second X-ray source for producing a second pencil beam of X-rays directed toward said human body and a second detector assembly providing a signal representative of the intensity of the X-rays scattered from said human body as a result of being scanned by said second X-ray source, said second detector assembly being disposed on a same side of said human body as said second X-ray source and having an active area for receiving a portion of said scattered X-rays from said human body as a result of being scanned by said second X-ray source and a portion of transmitted X-rays from the first module, wherein said signals generated from said first detector assembly and said second detector assembly are processed to form at least one image, and wherein the first module or the second module move vertically while said human body remains stationary.

2. The imaging apparatus of claim 1, further comprising an enclosure having four walls.

3. The imaging apparatus of claim 2, further comprising at least one ceiling and at least one floor.

4. The imaging apparatus of claim 1 wherein said first X-ray source of said first module scans the human body while the second X-ray source is not activated.

5. The imaging apparatus of claim 1 wherein said second X-ray source of said second module scans the human body while the first X-ray source is not activated.

6. The imaging apparatus of claim 1 wherein the vertical movement of the first module and the second module is coordinated.

7. The imaging apparatus of claim 1 including a processor adapted to process signals representative of the intensity of the X-rays scattered from said human body as a result of being scanned by the first X-ray source from the first detector assembly and signals representative of the intensity of the X-rays scattered from said human body as a result of being scanned by the second X-ray source from the second detector assembly to generate at least one image.

8. The imaging apparatus of claim 1 including a processor adapted to process signals representative of the intensity of the transmitted X-rays from the first module to form a shadow image of the human body.

9. The imaging apparatus of claim 1 including a processor adapted to process signals representative of the intensity of the transmitted X-rays from the second module to form a shadow image of the human body.

10. The imaging apparatus of claim 1 wherein the first module and the second module sequentially scan the human body.

11. The imaging apparatus of claim 1 wherein the first module and the second module move vertically in a synchronous manner such that, while the first detector assembly captures backscattered signals, the second detector assembly captures transmitted signals that are not absorbed or backscattered by the human body.

12. The imaging apparatus of claim 1 wherein the first module and the second module move vertically in a synchronous manner such that, while the second detector assembly captures backscattered signals, the first detector assembly captures transmitted signals that are not absorbed or backscattered by the human body.

13. The imaging apparatus of claim 1, further comprising a display for presenting said at least one image to an operator.

* * * * *

UNITED STATES PATENT AND TRADEMARK OFFICE
CERTIFICATE OF CORRECTION

PATENT NO. : 9,020,100 B2  
APPLICATION NO. : 14/057564  
DATED : April 28, 2015  
INVENTOR(S) : Richard Mastronardi et al.

Page 1 of 1

It is certified that error appears in the above-identified patent and that said Letters Patent is hereby corrected as shown below:

On title page, item 73 Assignee,
replace "America Science and Engineering, Inc."
with "American Science and Engineering, Inc."

Signed and Sealed this
Eighteenth Day of August, 2015

Michelle K. Lee
*Director of the United States Patent and Trademark Office*